United States Patent
Schilling

(10) Patent No.: US 9,012,169 B2
(45) Date of Patent: *Apr. 21, 2015

(54) METABOLIC METHOD TO IDENTIFY COMPOUNDS HAVING FLAVOR OR FRAGRANCE

(75) Inventor: Boris Schilling, Knonau (CH)

(73) Assignee: Givaudan S.A., Vernier (CH)

( * ) Notice: Subject to any disclaimer, the term of this patent is extended or adjusted under 35 U.S.C. 154(b) by 1321 days.

This patent is subject to a terminal disclaimer.

(21) Appl. No.: 11/632,977

(22) PCT Filed: Jul. 15, 2005

(86) PCT No.: PCT/CH2005/000411
§ 371 (c)(1),
(2), (4) Date: May 2, 2007

(87) PCT Pub. No.: WO2006/007751
PCT Pub. Date: Jan. 26, 2006

(65) Prior Publication Data
US 2008/0166735 A1    Jul. 10, 2008

Related U.S. Application Data

(60) Provisional application No. 60/590,409, filed on Jul. 21, 2004.

(51) Int. Cl.
| | | |
|---|---|---|
| *C07K 14/705* | (2006.01) | |
| *C12Q 1/26* | (2006.01) | |
| *C12Q 1/28* | (2006.01) | |
| *C12Q 1/32* | (2006.01) | |
| *C12Q 1/34* | (2006.01) | |
| *C12Q 1/44* | (2006.01) | |
| *C12Q 1/48* | (2006.01) | |

(52) U.S. Cl.
CPC ............ *C07K 14/705* (2013.01); *C12Q 1/26* (2013.01); *C12Q 1/28* (2013.01); *C12Q 1/32* (2013.01); *C12Q 1/34* (2013.01); *C12Q 1/44* (2013.01); *C12Q 1/48* (2013.01)

(58) Field of Classification Search
None
See application file for complete search history.

(56) References Cited

U.S. PATENT DOCUMENTS 5,993,778 A * 11/1999 Firestein et al. ............... 424/9.1
7,638,343 B2 * 12/2009 Schilling ....................... 436/181

OTHER PUBLICATIONS

Chen Y. et al. Immunoblot analysis and immunohistochemical characterization of CYP2A expression in human olfactory mucosa, Biochemical Pharmacology, 2003, vol. 66, No. 7, pp. 1245-1251.*
Pollien P. et al. Hyphenated headspace-gas chromatography-sniffing technique: screening of impact odorants and quantitative aromagram comparisons, J. Agric. Food Chem., 1997, vol. 45, pp. 2630-2637.*
Zhang R. et al. Design, synthesis and evaluation of novel P450 fluorescent probes bearing alpha-cyanoether, Tetrahedron Letters, 2003, vol. 44, pp. 4331-4334.*
Spracklin D.K. et al., Human Reductive Halothane Metabolism in Vitro Is Catalyzed by Cytochrome P450 2A6 and 3A4, Drug Metabolism and Disposition, 1996, vol. 24, No. 9, pp. 976-983.*
CDC Brochure N-nitrosodiethylamine; on the web at—http://www.cdc.gov/niosh/npg/npgd0461.html; published and last updated on Nov. 18, 2010, pp. 1-2; accessed on Sep. 26, 2013.*

* cited by examiner

*Primary Examiner* — Satyendra Singh
(74) *Attorney, Agent, or Firm* — Curatolo Sidoti Co., LPA; Joseph G. Curatolo; Salvatore A. Sidoti

(57) ABSTRACT

The invention is concerned with the identification of compounds as flavors or fragrances, their precursors, or as modulators of the perception of fragrances or flavors. The method comprises a reaction of a compound with a metabolic enzyme expressed in the nose, mouth or respiratory tract, followed by a method of identification of the compound or its metabolites as a fragrance or flavor, their precursor, or a modulator of their perception or of the perception of their respective leads.

11 Claims, No Drawings

METABOLIC METHOD TO IDENTIFY COMPOUNDS HAVING FLAVOR OR FRAGRANCE

CROSS REFERENCE TO RELATED APPLICATIONS

This application is a national stage application under 35 U.S.C. §371 of International Application No. PCT/CH2005/000411, filed 15 Jul. 2005, which claims the benefit of the Filing date of U.S. Provisional Application Serial No. 60/590,409, filed 21 Jul. 2004, from which application priority is claimed.

BACKGROUND

The invention relates to methods of identifying compounds useful in the field of flavours and fragrances, and to the corresponding lead structures of these compounds. Said methods comprise a reaction with a metabolic enzyme. The invention also relates to the identification of metabolic enzymes and their use in said methods.

Compounds useful in the field of flavours and fragrances may be flavour compounds and fragrance compounds as such, but also modulators of fragrance and flavour perception. Such modulators include enhancers and masking agents of the olfactory and gustatory senses, and regulators or modulators of metabolic reactions involving aforementioned compounds occurring in the respiratory tract, in particular in the oral and/or nasal cavity.

Flavour and fragrance compounds reach the oral and nasal cavity where they may cause the perception of flavour and fragrance compounds by binding to olfactory and/or gustatory receptors. Binding to a receptor will lead to perception if the receptor is activated and initiates a signal transduction cascade that, if successfully transmitted, leads to the flavour or fragrance signal being perceived.

For olfactory receptors, almost 1000 genes have been identified on human chromosomes and it is speculated that approximately 350 different functional receptor proteins are present in the human nose to detect a plethora of odorous compounds. Typically, an odorant reaches the olfactory epithelium to bind and activate olfactory receptors.

The use of olfactory and gustatory receptors in in vitro chemoreceptor screening methods to identify new flavour and fragrance compounds and lead structures is known and described for example in WO9217585, WO02059349, US20020064817, WO0127158. In these screening methods, chemoreceptors are exposed to compounds and identify receptor ligands based on the interaction of a compound with an olfactory or gustatory receptor of interest.

However, known screening methods identify compounds or leads that in many cases turn out to be not relevant.

It has been speculated that compounds may undergo enzymatic metabolism in the respiratory tract and in the oral and nasal cavity, and form derivatives with altered chemical, physical and biological properties. Enzymatic metabolism has not yet been shown in the human olfactory epithelium in vivo, and only a small number of genes encoding metabolic enzymes have been previously reported to be expressed in the human nose or oral cavity (carboxyl esterase enzymes, a UDP-glucuronosyltransferase UGT2A1, and cytochrome P450 enzyme CYP2A13).

Receptor ligands identified by known in vitro receptor screens are not necessarily perceived as fragrance or flavour. Whether a ligand actually triggers fragrance or flavour perception in the human nose depends on the fate of the ligand which may depend on the occurrence of metabolism. By the action of a metabolic enzyme, the ligand may react to a compound that will not bind any receptors and is not perceived by the human senses at all. Furthermore, another receptor ligand may be generated to account for a different quality of perception, which makes it very difficult to find lead structures.

Metabolism of such compounds that are substrate of an enzyme present in the oral or nasal cavity or the respiratory tract may occur after receptor activation, or may occur prior to receptor binding in the fluidic mucus or in cells lining the cavity. The metabolite(s) may have chemical and/or physical properties which are of advantage for interaction with receptors, other enzymes and/or odorant binding proteins. Substrates may be odorant compounds or non-odorant compounds. In case of the latter, one or more metabolite of said substrate may be an odorant, and/or have the above-mentioned properties.

Metabolism may inactivate or activate receptor ligands. Fragrance and flavour compounds may be agonists, antagonists, enzyme substrates, enzyme inhibitors, and allosteric regulators of receptors or enzymes. The metabolites may compete for example for receptor binding, interact with additional receptors and enzymes, and/or modulate the activity and sensitivity of receptors and enzymes and components of the signal transduction cascade, including cyclic nucleotide-gated (CNG) channels of olfactory sensory neurons. The metabolites generated from substrates of metabolic enzymes may have properties which enable them to interact with receptors and enzymes and these metabolites may in fact be primarily responsible for the perceived quality and effects of flavour and fragrance ingredients and/or compete with their substrates for receptor interaction, and in particular for receptor activation.

Depending on the occurrence of enzymatic metabolism in the oral or nasal cavity or the respiratory tract, known in vitro chemoreceptor screening methods may result in false positive or false negative results when trying to identify fragrances or flavours. For example, a ligand identified by the screening method may be rapidly metabolised in the human nose to a non-olfactive compound (false positive result). Another problem occurs if a compound that is not a ligand to a chemoreceptor itself but is metabolised in the human nose to result in a ligand for a chemoreceptor, i.e. a precursor. The precursor will give a negative signal when applying known screening methods (false negative result). These possibilities are further illustrated below for an olfactive compound "A".

Compound "A" has a particular olfactive note described by a perfumer. A is metabolised to compound "B" in the nose and B is responsible for the particular note, by activating one or several olfactory receptors which are required to perceive the smell as described by the perfumer. In an in vitro receptor screen performed with A (precursor), the receptors responding to B are not activated and will not be identified. The screen will either give a correct negative result for A while failing to identify receptors responding to B ("failed identification"), or identify receptors which respond to A but are not relevant since A is metabolised to B ("false positive results"). Known screens show the correct structure-activity relationship. However, the identified compound may still be irrelevant regarding the perception as fragrance, so that the screen will not indicate a correct relationship between structure and fragrance perception. This will make subsequent identification, for example on the basis of lead structures, difficult or impossible.

Even if a compound is correctly identified by a conventional receptor screen it may be very difficult to find the relevant lead compounds on the basis of these results, since the lead may be incorrect and misleading. The example below illustrates this.

A compound "C" may be partially metabolised in the human nose to form compound "D", both compounds being present in the nose in parallel. "C" and "D" may have different olfactive notes, which may account for the broad olfactive description assigned to some single fragrance or flavour compounds. Known screening methods to identify flavours and fragrances make lead finding for particular olfactive notes very difficult, since the identified ligand may not be responsible for the fragrance or flavour perception in the human nose at all. Therefore lead compounds identified for particular olfactive notes may not be the relevant ones.

SUMMARY

The present invention overcomes the above-described deficiencies of known screening methods by providing a metabolic method to identify compounds useful in the field of fragrances and flavours. This allows for an effective identification of said compounds and their lead structures. Further it allows the identification of modulators of the perception of a fragrance or flavour, including enhancers and masking agents of the olfactory and gustatory senses, and including regulators or modulators of metabolic reactions in the oral and/or nasal cavity. It also allows identification of compounds as precursors of flavours and fragrances or modulators of chemosensory perception.

The invention therefore provides a method of identifying a compound or its metabolite as a flavour or fragrance, or as a modulator of the perception of a fragrance or flavour, comprising a reaction of a compound with a metabolic enzyme selected from the group consisting of the enzymes of Table 1 and 2 listed herein-below, followed by a method of identifying the compound or at least one of its metabolites as a fragrance or flavour or a modulator.

DETAILED DESCRIPTION

Enzymes useful in metabolic reactions according to the invention are enzymes expressed in at least one of following: the nasal cavity, the oral cavity, the respiratory tract, preferably in the olfactory mucosa, the respiratory mucosa and the oral mucosa, most preferably in the olfactory mucosa. Enzymes expressed and present in the cells lining those regions and their fluids (mucus, saliva) that are in contact with the air when breathing are preferred. The nasal cavity is lined with olfactory mucosa, respiratory mucosa, squamous epithelium and transitional epithelium. The olfactory mucosa is particularly specialised for the perception of odorants due to the presence of olfactory epithelium containing olfactory receptor-expressing neurons. Most preferred enzymes may be selected by their expression in cells that are contained in the olfactory epithelium comprising the sustentacular cells, the duct cells of Bowman's glands, and the progenitor basal cells.

Groups of human enzymes useful in the present invention include epoxide hydrolases, esterases, flavin-containing monooxygenases, glutathione peroxidases, glutathione reductases, glutathione synthase, glutathione S-transferases, glutathione lyases, oxidases, peroxidases, epoxidases, reductases, rhodanese enzymes, sulfatases, sulfotransferases, UDP-glucuronosyltransferases (UGTs) and oxygenases.

Preferred human enzymes that may be employed in the present invention include Flavin-Containing Monooxygenases (FMOs), UGTs, Amine Oxidases (AOs, including MAOs, particularly MAO-A and -B), Cytochrome P450 enzymes (CYPs), Microsomal Epoxide Hydrolase (EH), and Carboxyl Esterase (CE).

Further enzymes that may be useful in methods of the present invention are Arylamine N-Acetyltransferases (NAT), NAT1 and NAT2.

Many of the above enzymes and any necessary partner enzymes and/or coenzymes or cofactors may be purchased from BD Biosciences, San Jose, Calif., USA, from Invitrogen life Technologies Carlsbad, Calif., USA, or from Sigma-Aldrich, St. Louis, Mo., USA.

For example, CYP enzymes need as a partner enzyme the corresponding reductase enzyme which is the NADPH-dependent cytochrome P450 reductase (POR). Furthermore, the additional presence of a Cytochrome b5 (b5) may be advantageous. POR and b5 are commercially available at the above mentioned sources as well. Methods and conditions for CYP enzymes are described for example in Yamazaki et al. (1999) *J. Chromatography B,* 721:13-19; and in Gu et al. (1998) *JPET,* 285:1287-1295. An overview on CYP expression systems is described for example in Gonzalez and Korzekwa (1995) *Annu. Rev. Phamacol. Toxicol.,* 35:369-390.

For some enzymatic reactions, cofactors are necessary, as is well known in the art. NADPH is required for the measurement of oxidase activity catalyzed by P450s, FMOs, NADPH-P450 reductase, and many other oxidase enzymes. A common source of NADPH in an oxidase enzyme assay is an NADPH regenerating system that generates NADPH in situ using an enzymatic reaction. For example, glucose-6-phosphate dehydrogenase (G6PDH) will convert NADP+ to NADPH in the presence of the substrate glucose-6-phosphate (Glc-6-PO4).

For UGTs, the measurement of glucuronidation activity catalyzed by microsomes, S9 and recombinant UGT enzymes requires an appropriate incubation buffer system containing UDP-glucuronic acid (UDPGA), an essential UGT enzyme cofactor that is available from BD Biosciences, San Jose, Calif., USA.

NATs are cytosolic proteins that play an important role in the N-acetylation of compounds containing aromatic amine and hydrazine groups, converting them to aromatic amides and hydrazides, respectively. Acetyl-coenzyme A (NAT cofactor) contributes the activated acetyl group required for NAT acetylation activity. Humans contain two functional NAT isoforms (NAT1 and NAT2). Several polymorphisms have been reported for the NAT enzymes, particularly NAT2.

Reaction conditions for NATs are known and for example described in Rogers et al. (1998) *Drug Metabolism and Disposition,* 26:502-505, Substrate selectivity of mouse N-acetyltransferases 1, 2, and 3 expressed in COS-1 cells; Grant et al. (2000) *Pharmacology,* 61:204-211, Pharmacogenetics of human arylamine N-acetyltransferases; Ilett et al. (1999) *Drug Metabolism and Disposition,* 27:957-959, 1998 International meeting of the arylamine N-acetyltransferases: Synopsis of the workshops on nomenclature, biochemistry, molecular biology, interspecies comparisons, and role in human disease risk; and deBethizy and Hayes (2001) Metabolism: A determinant of toxicity. In: *Principles and Methods of Toxicology,* ed. Hayes, A. W., p. 77-136.

For those enzymes not yet commercially available, the gene may be cloned and the gene expressed by methods well known in the art to produce the protein, i.e. the enzyme, see example 1 for production of CYP2A13. An overview on the heterologous expression of human metabolizing enzymes is also described in Guengerich et al. (1997) *Drug Metab. and Disp.,* 25:1234-1241.

A preferred group of enzymes are Cytochrome P450 enzymes (CYPs). CYPs represent a family of structurally characteristic mono-oxygenases. They constitute a superfamily of heme-thiolate enzymes, which catalyze primarily mono-oxygenase reactions involving a two-stage reduction of molecular oxygen and subsequent single-oxygen atom insertion into substrate molecules, although reductive metabolism is also known.

CYP enzymes are oxidoreductases (group EC 1), that are acting on paired donors, with incorporation or reduction of molecular oxygen (group EC 1.14), and with reduced flavin or flavoprotein as one donor, and incorporation of one atom of oxygen (EC 1.14.14), and belonging to the group of unspecific monooxygenases (EC 1.14.14.1). Oxidoreductases are acting on paired donors with incorporation of molecular oxygen with reduced flavin or flavoprotein as one donor, and incorporation of one atom of oxygen. These group of unspecific monooxygenases is also known as microsomal monooxygenases, xenobiotic monooxygenases, aryl-4-monooxygenase, aryl hydrocarbon hydroxylase, microsomal P-450, flavoprotein-linked monooxygenases, or flavoprotein monooxygenases. The general reaction scheme is the following: RH+reduced flavoprotein+O2=>ROH+oxidized flavoprotein+H2O; with RH, reduced flavoprotein and O2 being the substrates and ROH, oxidized flavoprotein and H2O being the products.

This group of heme-thiolate proteins (CYP or P450) are acting on a wide range of substrates including many xenobiotics, steroids, fatty acids, vitamins and prostaglandins; reactions catalysed include hydroxylation, epoxidation, N-oxidation, sulfooxidation, N-, S- and O-dealkylations, desulfation, deamination, and reduction of azo, nitro and N-oxide groups. Together with cytochrome P450 oxidoreductase (POR), EC 1.6.2.4, it forms a system in which two reducing equivalents are supplied by NADPH.

When complexed with carbon monoxide, the reduced heme protein exhibits a characteristic absorbance at 450 nm which gave the enzyme family its name. Structures and mechanisms of these enzymes are well-known in the art, compare for example Sligar (1999) *Essays in Biochemistry* 34:71-83; Ortiz de Montellano (1995) Cytochrome P450: Structure, Mechanism, and Biochemistry (2nd edition) Plenum Press, New York).

Enzymes commercially available from BD Biosciences (BD Gentest™), Invitrogen life technologies or Sigma-Aldrich that may be useful in the present invention include the following: CYP1A1, CYP1A2, CYP1B1, CYP2B4, CYP2A6, CYP2B6, CYP2C8, CYP2C9, CYP2C9*1, CYP2C9*2, CYP2C9*3, CYP2C18, CYP2C19, CYP2D6, CYP2D6*1, CYP2D6*10, CYP2E1, CYP2J2, CYP3A4, CYP3A5, CYP3A7, CYP4A, CYP4A11, CYP4F2, CYP4F3A, CYP4F3B, CYP4F12, CYP19, CYP2C39.

We have found the following genes of such enzymes to be expressed in the nasal mucosa and the corresponding enzymes are particularly preferred in methods according to the present invention (see Table 1).

TABLE 1

Genes of metabolic enzymes which are expressed in the human olfactory mucosa and may be employed in methods according to the present invention

| NCBI Identifier and/or GeneBank Number | Encoded proteins (enzyme subunits) or enzymes |
|---|---|
| Dehydrogenases | |
| BC008185 | Human short-chain alcohol dehydrogenase |
| M12963 | Human alcohol dehydrogenase class I alpha subunit (ADH1) |
| X03350 | Human alcohol dehydrogenase class I beta subunit |
| M12272 | Human alcohol dehydrogenase class I gamma subunit (ADH3) |
| M81118 | Human alcohol dehydrogenase chi polypeptide (ADH5) gene |
| K03000 | Human aldehyde dehydrogenase (ALDH1) |
| U46689 | Human microsomal aldehyde dehydrogenase (ALDH10) |
| U07919 | Human aldehyde dehydrogenase (ALDH6) |
| U10868 | Human aldehyde dehydrogenase (ALDH7) |
| U37519 | Human aldehyde dehydrogenase (ALDH8) |
| X05409 | Human mitochondrial aldehyde dehydrogenase I (ALDH I, EC 1.2.1.3) |
| M74542 | Human aldehyde dehydrogenase type III (ALDH III) |
| U34252 | Human gamma-aminobutyraldehyde dehydrogenase (ALDH9) |
| M93405 | Human methylmalonate semialdehyde dehydrogenase gene |
| AL031230 | NAD+-dependent succinic semialdehyde dehydrogenase (SSADH, EC 1.2.1.24) |
| Cytochrome P450's | |
| U03688 | Human cytochrome P450 (CYP1B1) |
| M14565 | Human cytochrome P450scc (CYP11A1) |
| U22028 | Human cytochrome P450 (CYP2A13) |
| NM_000762 | Human cytochrome P450(CYP2A6) |
| U22029 | Human cytochrome P450 (CYP2A7) |
| M29874 | Human cytochrome P450 (CYP2B1) |
| M61855 | Human cytochrome P450 (CYP2C9) |
| X16867 | Human cytochrome P450 (P450 IID) |
| U37143 | Human cytochrome P450 (CYP2J2) |
| D00408 | Human cytochrome P450 (P450 HFLa) |
| BC017758 | Human cytochrome P450 (CYP4B1Ser207) |
| U23942 | Human cytochrome P450 (CYP51) |
| J02843 | Human cytochrome P450 (CYP2E1) |
| NM_000774 | Human cytochrome P450 (CYP2F1) |

TABLE 1-continued

Genes of metabolic enzymes which are expressed in the human olfactory mucosa and may be employed in methods according to the present invention

| NCBI Identifier and/or GeneBank Number | Encoded proteins (enzyme subunits) or enzymes |
|---|---|
| Epoxide Hydrolases | |
| L05779 | Human cytosolic epoxide hydrolase |
| L25879 | *Homo sapiens* p53/HEH epoxide hydrolase (EPHX), mEH1 |
| Esterase | |
| L07765 | Human carboxylesterase |
| Flavin-containing Monooxygenase | |
| AL021026 | Human flavin-containing monooxygenase 3 (FMO3) |
| M64082 | Human flavin-containing monooxygenase 1 (FMO1) |
| AL021026 | Human flavin-containing monooxygenase 2 (FMO2) |
| M83772 | Human flavin-containing monooxygenase form II |
| Z11737 | *H. sapiens* mRNA for flavin-containing monooxygenase 4 (FMO4) |
| Z47553 | *H. sapiens* mRNA for flavin-containing monooxygenase 5 (FMO5) |
| Glutathione Peroxidase, Reductase, Synthase, S-transferase | |
| X13709 | Human glutathione peroxidase |
| X71973 | Human phospholipid hydroperoxide glutathione peroxidase (GPx-4) |
| X53463 | Human glutathione peroxidase-like protein |
| X15722 | Human glutathione reductase (EC 1.6.4.2) |
| U34683 | Human glutathione synthetase |
| D00632 | Human glutathione peroxidase |
| M16594 | Human glutathione S-transferase Ha subunit 2 (GST) |
| U12472 | Human glutathione S-transferase (GST phi) gene |
| X08020 | Human glutathione S-transferase subunit 4 (EC 2.5.1.18) |
| U90313 | Human glutathione-S-transferase homolog |
| AF025887 | Human glutathione S-transferase A4-4 (GSTA4) |
| J05459 | Human glutathione transferase M3 (GSTM3) |
| M96233 | Human glutathione transferase class mu number 4 (GSTM4) |
| U21689 | Human glutathione S-transferase-P1c |
| L38503 | Human glutathione S-transferase theta 2 (GSTT2) |
| U86529 | Human glutathione transferase Zeta 1 (GSTZ1) |
| D13315 | Human lactoyl glutathione lyase |
| U77604 | Human microsomal glutathione S-transferase 2 (MGST2) |
| AF026977 | Human microsomal glutathione S-transferase 3 (MGST3) |
| Oxidases | |
| AB012943 | Human amine oxidase, retina-specific (AOC2) |
| D16611 | Human coproporphyrinogen oxidase |
| U11863 | Human diamine oxidase, copper/topa quinone containing (DAO2) |
| U39447 | Human copper monamine oxidase |
| M68840 | Human monoamine oxidase A (MAO A) |
| M69177 | Human monoamine oxidase B (MAO B) |
| U60205 | Human methyl sterol oxidase (ERG25) |
| M19507 | Human myeloperoxidase |
| U39573 | Human salivary peroxidase |
| D78130 | Human squalene epoxidase |
| L31573 | Human sulfite oxidase |
| U39487 | Human xanthine dehydrogenase/oxidase |
| NM_148923 | Human cytochrome b5 (CYB5) |
| Reductases | |
| J03826 | Human adrenodoxin reductase |
| AF026947 | Human aflatoxin aldehyde reductase AFAR |
| J04794 | Human aldehyde reductase (ALDR1) |
| AB003151 | Human carbonyl reductase (CBR) |
| AB003151 | Human carbonyl reductase 3 (CBR3) |
| M28713 | Human NADH-cytochrome b5 reductase (b5R) |
| AF034544 | Human delta7-sterol reductase |
| L13278 | Human zeta-crystallin/quinone reductase |
| M81600 | Human NAD(P)H-quinone oxireductase |
| AY299456 | Human quinone oxidoreductase2 (NQO2) |
| U13395 | Human oxidoreductase (HHCMA56) |
| AF061741 | Human retinal short-chain dehydrogenase/reductase retSDR1 |
| M32313 | Human steroid 5-alpha-reductase |
| X91247 | Human thioredoxin reductase |
| NM_000941 | Human P450 reductase |

TABLE 1-continued

Genes of metabolic enzymes which are expressed in the human olfactory mucosa and may be employed in methods according to the present invention

| NCBI Identifier and/or GeneBank Number | Encoded proteins (enzyme subunits) or enzymes |
|---|---|
| Rhodanese | |
| D87292 | Human rhodanese |
| X59434 | Human rohu rhodanese |
| Sulfatase | |
| AF050145 | Human iduronate-2-sulfatase (IDS) |
| L13329 | Human iduronate-2-sulfatase (IDS) |
| Sulfotransferases | |
| AF019386 | Human heparan sulfate 3-O-sulfotransferase-1 precursor (3OST1) |
| X78283 | Human aryl sulfotransferase (ST1A3) |
| U36601 | Human heparan N-deacetylase/N-sulfotransferase-2 |
| AB003791 | Human keratan sulfate Gal-6-sulfotransferase |
| AF070594 | Human sulfotransferase (clone 24570 HNK-1) |
| AB020316 | Human dermatan/chondroitin sulfate 2-sulfotransferase |
| AB017915 | Human chondroitin 6-sulfotransferase |
| U34804 | Human thermostable phenol sulfotransferase (STP2) |
| U92315 | Human hydroxysteroid sulfotransferase SULT2B1b (HSST2) |
| AF038009 | Human tyrosylprotein sulfotransferase-1 |
| AF049891 | Human tyrosylprotein sulfotransferase-2 |
| UDP-Glucuronosyltransferases | |
| J05428 | Human 3,4-catechol estrogen UDP-glucuronosyltransferase |
| AJ006054 | Human UDP glucuronosyltransferase |
| X63359 | Human UDP glucuronosyltransferase (UGT2B10) |
| U08854 | Human UDP glucuronosyltransferase precursor (UGT2B15) |

*Representative Public Identifyer: National Center for Biotechnology Information (NCBI) and/or GeneBank Accession Number.

Furthermore, enzymes expressed from the following genes may be useful in methods of the present invention, compare tables 2 to 4 below. Useful enzymes that are expressed in the respiratory tract, in particular in the lung tissue and/or the nasal mucosa, are summarised in Table 2. Metabolism occurring in the respiratory tract, for example in the lung tissue, may influence retronasal olfactory sensation by exchange of air passing through the respiratory tract including the nose whereby metabolites formed by lung enzymes may reach the olfactory mucosa and receptors located therein.

TABLE 2

Genes of CYP enzymes, which are expressed in the respiratory tissue and may be useful in methods according to the present invention.

| CYP's | NCBI identifier |
|---|---|
| CYP1A1 | U03688 |
| CYP1A2 | NM_000761 |

TABLE 2-continued

Genes of CYP enzymes, which are expressed in the respiratory tissue and may be useful in methods according to the present invention.

| CYP's | NCBI identifier |
|---|---|
| CYP2B6 | NM_000767 |
| CYP2C8 | BC020596 |
| CYP2C18 | NM_000772 |
| CYP2D6 | NM_000106 |
| CYP2S1 | NM_030622 |
| CYP3A4 | NM_017460 |
| CYP3A5 | NM_000777 |

The cDNA sequences of the genes above are available at the National Centre for Biotechnology Information (NCBI) database, under the official identifiers given above. These are usually conterminous with the GeneBank accession Number.

Metabolic enzymes may further be selected from polymorphic variants of the enzymes mentioned above, for example the ones indicated in the tables below (see tables 3 and 4).

TABLE 3

Polymorphic enzymes corresponding to enzymes expressed in the human nose as shown above that may be useful in methods according to the present invention. The first column indicates particular amino acids, which are present in a common allele; the second column indicates the amino acid changes, which were identified in polymorphic alleles

| Enzymes/amino acids | polymorphism | Polymorphic Enzyme |
|---|---|---|
| CYP2A13 | | |
| Gly144 | Arg144 | (CYP2A13) |
| Arg257 | Cys257 | (CYP2A13) |
| Arg25 | Gln25 | (CYP2A13) |
| Arg30, Leu33 | Lys30, Val33 | (CYP2A13) |

TABLE 3-continued

Polymorphic enzymes corresponding to enzymes expressed in the human nose as shown above that may be useful in methods according to the present invention. The first column indicates particular amino acids, which are present in a common allele; the second column indicates the amino acid changes, which were identified in polymorphic alleles

| Enzymes/amino acids | polymorphism | Polymorphic Enzyme |
| --- | --- | --- |
| Arg25, Arg257 | Gln25, Cys257 | CYP2A13.2 |
| Asp158 | Glu158; insertion of Thr after 133 | CYP2A13.3 |
| Arg101 | Gln101 | CYP2A13.4 |
| Phe453 | Tyr453 | CYP2A13.5 |
| Arg494 | Cys494 | CYP2A13.6 |
| Arg101 | Premature termination (stop) 101 | CYP2A13.7 |
| Asp158 | Glu158 | CYP2A13.8 |
| Val323 | Leu323 | CYP2A13.9 |
| CYP2A6 | | |
| Leu160 | His160 | CYP2A6.2 |
| Gly479 | Val479 | CYP2A6.5 |
| Arg128 | Gln128 | CYP2A6.6 |
| Ile471 | Thr471 | CYP2A6.7 |
| Arg485 | Leu485 | CYP2A6.8 |
| I471, Arg485 | Thr471, Leu485 | CYP2A6.10 |
| Ser224 | Pro224 | CYP2A6.11 |
| 10 aa substit. from CYP2A7 | Oscarson et al. (2002) Hum. Mutat. 20: 275-283 | CYP2A6.12 |
| Gly5 | Arg5 | CYP2A6.13 |
| Ser29 | Asn29 | CYP2A6.14 |
| Lys194 | Glu194 | CYP2A6.15 |
| Arg203 | Ser203 | CYP2A6.16 |
| Glu419 | Asp419 | (CYP2A6) |
| Val365 | Met365 | CYP2A6.17 |
| Tyr392 | Phe392 | CYP2A6.18 |
| Tyr392, Ile471 | Phe392, Thr471 | CYP2A6.19 |
| Lys476 | Arg476 | CYP2A6.21 |
| Asp158, Leu160 | Glu158, Ile160 | CYP2A6.22 |
| CYP1B1 | | |
| Arg48, Ala119 | Gly48, Ser119 | CYP1B1.2 |
| Leu432 | Val432 | CYP1B1.3 |
| Asn453 | Ser453 | CYP1B1.4 |
| Arg48, Leu432 | Gly48, Val432 | CYP1B1.5 |
| Arg48, Ala119, Leu432 | Gly48, Ser119, Val432 | CYP1B1.6 |
| Arg48, Ala119, Leu432, Ala443 | Gly48, Ser119, Val432, Gly443 | CYP1B1.7 |
| Trp57 | Cys57 | CYP1B1.11 |
| Gly61 | Glu61 | CYP1B1.12 |
| Gly365 | Trp365 | CYP1B1.18 |
| Pro379 | Leu379 | CYP1B1.19 |
| Glu387 | Lys387 | CYP1B1.20 |
| Arg390 | His390 | CYP1B1.21 |
| Pro437 | Leu437 | CYP1B1.23 |
| Arg469 | Trp469 | CYP1B1.25 |
| CYP2C9 | | |
| Arg144 | Cys144 | CYP2C9.2 |
| Ile359 | Leu359 | CYP2C9.3 |
| Ile359 | Thr359 | CYP2C9.4 |
| Asp360 | Glu360 | CYP2C9.5 |
| Leu19 | Ile19 | CYP2C9.7 |
| Arg150 | His150 | CYP2C9.8 |
| His251 | Arg251 | CYP2C9.9 |
| Glu272 | Gly272 | CYP2C9.10 |
| Arg335 | Trp335 | CYP2C9.11 |
| Pro489 | Ser489 | CYP2C9.12 |
| Arg125 | His125 | CYP2C9.14 |
| Thr299 | Ala299 | CYP2C9.16 |
| Pro382 | Ser382 | CYP2C9.17 |
| Ile359, Asp397 | Leu359, Ala397 | CYP2C9.18 |
| Gln454 | His454 | CYP2C9.19 |
| Gly70 | Arg70 | CYP2C9.20 |
| CYP2E1 | | |
| Arg76 | His76 | CYP2E1.2 |
| Val389 | Ile389 | CYP2E1.3 |
| Val179 | Ile179 | CYP2E1.4 |
| CYP2J2 | | |
| Thr143 | Ala143 | CYP2J2.2 |
| Arg158 | Cys158 | CYP2J2.3 |
| Ile192 | Asn192 | CYP2J2.4 |

TABLE 3-continued

Polymorphic enzymes corresponding to enzymes expressed in the human nose as shown above that may be useful in methods according to the present invention. The first column indicates particular amino acids, which are present in a common allele; the second column indicates the amino acid changes, which were identified in polymorphic alleles

| Enzymes/amino acids | polymorphism | Polymorphic Enzyme |
| --- | --- | --- |
| Asp342 | Asn342 | CYP2J2.5 |
| Asn404 | Tyr404 | CYP2J2.6 |
| Gly312 | Arg312 | CYP2J2.8 |
| Pro351 | Leu351 | CYP2J2.9 |
| CYP4B1 | | |
| Arg173 | Trp173 | CYP4B1.3 |
| Ser322 | Gly322 | CYP4B1.4 |
| Met331 | Ile331 | CYP4B1.5 |
| Arg173; Val345 | Trp173; Ile345 | CYP4B1.6 |
| | Nucleotides 881-882 (A-T) deleted, resulting in premature termination (stop) | CYP4B1.7 |
| *Homo sapiens* p53/HEH epoxide hydrolase (EPHX), mEH1 (AAH08291) | | |
| His148, Lys348, Leu406, Leu420 | Asn148, Ser348, Phe406, Val420 | (EPHX) |
| Tyr113, His139 | His113, Arg139 | (EPHX) |
| Thr396 | Ile396 | (EPHX) |
| Carboxyl Esterase (AAA35711) | | |
| Gly56, Gly535 | Ala56, Ala535, insertion of Gln after Met361 | (CE) |
| Gly56, Gly535 | Ala56, Ala535, insertion of Ala after Thr17 | (CE) |
| Gly56, Gly535 | Ala56, Ala535, insertion of Gln after Met361, insertion of Ala after Thr17 | (CE) |
| | Insertion of Gln after Met361, insertion of Ala after Thr17 | (CE) |

TABLE 4

Polymorphic CYP enzymes expressed in the respiratory tract or the lung that may be useful in methods according to the present invention.

| | Polymorphisms | Polymorphic Enzyme |
| --- | --- | --- |
| CYP1A1 | | |
| Ile462 | Val462 | CYP1A1.2 |
| Thr461 | Asn461 | CYP1A1.4 |
| Arg464 | Ser464 | CYP1A1.5 |
| Met331 | Ile331 | CYP1A1.6 |
| Ile448 | Asn448 | CYP1A1.8 |
| Arg464 | Cys464 | CYP1A1.9 |
| Arg477 | Trp477 | CYP1A1.10 |
| Pro492 | Arg492 | CYP1A1.11 |
| CYP1A2 | | |
| Phe21 | Leu21 | CYP1A2.2 |
| Asp348 | Asn348 | CYP1A2.3 |
| Ile386 | Phe386 | CYP1A2.4 |
| Cys406 | Tyr406 | CYP1A2.5 |
| Arg431 | Trp431 | CYP1A2.6 |
| Thr83 | Met83 | CYP1A2.9 |
| Glu168 | Gln168 | CYP1A2.10 |
| Phe186 | Leu186 | CYP1A2.11 |
| Ser212 | Cys212 | CYP1A2.12 |
| Gly299 | Ser299 | CYP1A2.13 |
| Thr438 | Ile438 | CYP1A2.14 |
| CYP2B6 | | |
| Arg22 | Cys22 | CYP2B6.2 |
| Ser259 | Arg259 | CYP2B6.3 |
| Lys262 | Arg262 | CYP2B6.4 |
| Arg487 | Cys487 | CYP2B6.5 |
| Gln172; Lys262 | His172; Arg262 | CYP2B6.6 |
| Gln172; Lys262; Arg487 | His172; Arg262; Cys487 | CYP2B6.7 |
| Lys139 | Glu139 | CYP2B6.8 |

TABLE 4-continued

Polymorphic CYP enzymes expressed in the respiratory tract or the lung that may be useful in methods according to the present invention.

| Polymorphisms | | Polymorphic Enzyme |
|---|---|---|
| Gln172 | His172 | CYP2B6.9 |
| Pro167 | Ala167 | |
| Gln21, Arg22 | Leu21, Cys22 | CYP2B6.10 |
| Met46 | Val46 | CYP2B6.11 |
| Gly99 | Glu99 | CYP2B6.12 |
| Lys139, Gln172, Lys262 | Glu139, His172, Arg262 | CYP2B6.13 |
| Arg140 | Gln140 | CYP2B6.14 |
| Ile391 | Asn391 | CYP2B6.15 |
| CYP2C8 | | |
| Ile269 | Phe269 | CYP2C8.2 |
| Arg139; Lys399 | Lys139; Arg399 | CYP2C8.3 |
| Ile264 | Met264 | CYP2C8.4 |
| Gly171 | Ser171 | CYP2C8.6 |
| Arg186 | Gly186 | CYP2C8.8 |
| Lys247 | Arg247 | CYP2C8.9 |
| Lys383 | Asn383 | CYP2C8.10 |
| CYP2D6 | | |
| Arg296; Ser486 | Cys296; Thr486 | CYP2D6.2 |
| His324 | Pro324 | CYP2D6.7 |
| Lys281 | Amino acid deleted | CYP2D6.9 |
| Pro34; Ser486 | Ser34; Thr486 | CYP2D6.10 |
| Gly42; Arg296; Ser486 | Arg42; Cys296; Thr486 | CYP2D6.12 |
| Pro34; Gly169; Arg296; Ser486 | Ser34; Arg169; Cys296; Thr486 | CYP2D6.14A |
| Gly169; Arg296; S486 | Arg169; Cys296; Thr486 | CYP2D6.14B |
| Thr107; Arg296; Ser486 | Ile107; Cys296; Thr486 | CYP2D6.17 |
| | Insertion 468-470 (Val-Pro-Thr) | CYP2D6.18 |
| Arg28 | Cys28 | CYP2D6.22 |
| Ala85 | Val85 | CYP2D6.23 |
| Ile297 | Leu297 | CYP2D6.24 |
| Arg343 | Gly343 | CYP2D6.25 |
| Ile369 | Thr369 | CYP2D6.26 |
| Glu410 | Lys410 | CYP2D6.27 |
| Val7; Gln151; Arg296; Ser486 | Met7; Glu151; Cys296; Thr486 | CYP2D6.28 |
| Val136; Arg296; Val338; Ser486 | Met136; Cys296; M338; Thr486 | CYP2D6.29 |
| Arg296; Ser486 | Insertion 172-174 (Phe-Arg-Pro); Cys296; Thr486 | CYP2D6.30 |
| Arg296; Arg440; Ser486 | Cys296; His440; Thr486 | CYP2D6.31 |
| Arg296; Glu410; Ser486 | Cys296; Lys410; Thr486 | CYP2D6.32 |
| Als237 | Ser237 | CYP2D6.33 |
| Arg296 | Cys296 | CYP2D6.34 |
| Val11; Arg296; Ser486 | Met11; Cys296; Thr486 | CYP2D6.35 |
| Pro34; Ser486 | Ser34; Thr486 | CYP2D6.36 |
| Pro34; Arg201; Ser486 | Ser34; His201; Thr486 | CYP2D6.37 |
| Ser486 | Thr486 | CYP2D6.39 |
| Thr107; Arg296; Ser486 | Ile107; insertion 172-174 (Phe-Arg-Pro); Cys296; Thr486 | CYP2D6.40 |
| Arg26 | His26 | CYP2D6.43 |
| Glu155, Arg296, Ser486 | Lys155, Cys296, Thr486 | CYP2D6.45 |
| Arg26, Glu155, Arg296, Ser486 | His26, Lys155, Cys296, Thr486 | CYP2D6.46 |
| Arg25, Pro34, Ser486 | Trp25, Ser34, Thr486 | CYP2D6.47 |
| Ala90 | Val90 | CYP2D6.48 |
| Pro34; Phe120, Ser486 | Ser34, Ile120, Thr486 | CYP2D6.49 |
| Glu156 | Ala156 | CYP2D6.50 |
| Arg296, Glu334, Ser486 | Cys296, Ala334, Thr486 | CYP2D6.51 |
| Pro34, Glu418 | Ser34, Lys418 | CYP2D6.52 |
| CYP2S1 | | |
| Arg380 | Cys380 | CYP2S1.2 |
| Pro466 | Leu466 | CYP2S1.3 |
| CYP3A4 | | |
| Ser222 | Pro222 | CYP3A4.2 |
| Met445 | Thr445 | CYP3A4.3 |
| Ile118 | Val118 | CYP3A4.4 |
| Pro218 | Arg218 | CYP3A4.5 |
| Gly56 | Asp56 | CYP3A4.7 |
| Arg130 | Gln130 | CYP3A4.8 |
| Val170 | Ile170 | CYP3A4.9 |
| Asp174 | His174 | CYP3A4.10 |
| Thr363 | Met363 | CYP3A4.11 |
| Leu373 | Phe373 | CYP3A4.12 |

TABLE 4-continued

Polymorphic CYP enzymes expressed in the respiratory tract or the lung that may be useful in methods according to the present invention.

| | Polymorphisms | Polymorphic Enzyme |
|---|---|---|
| Pro416 | Leu416 | CYP3A4.13 |
| Leu15 | Pro15 | CYP3A4.14 |
| Arg162 | Gln162 | CYP3A4.15 |
| Thr185 | Ser185 | CYP3A4.16 |
| Phe189 | Ser189 | CYP3A4.17 |
| Leu293 | Pro293 | CYP3A4.18 |
| Pro467 | Ser467 | CYP3A4.19 |
| CYP3A5 | | |
| Thr398 | Asn398 | CYP3A5.2 |
| Gln200 | Arg200 | CYP3A5.4 |
| Arg28 | Cys28 | CYP3A5.8 |
| Ala337 | Thr337 | CYP3A5.9 |
| Phe446 | Ser446 | CYP3A5.10 |
| Ser100 | Tyr100 | (CYP3A5) |

Reaction with a Metabolic Enzyme: Without Competitive Standard Substrate

In one embodiment of the invention, a CYP metabolic enzyme (cytochrome P450 enzyme) is used in a method according to the invention.

CYP enzymes, either from human or animal source such as rat, are used in combination with human or rat P450 reductase.

Human or rat P450 reductase may be produced in insect cells alone or together with a CYP metabolic enzyme, for example as described by Caroline et al. (1996) Meth. Enzymol. 272:86-95, and references therein. Alternatively, it may be produced in Escherichia coli, for example as described by Shen et al. (1989), J. Biol. Chem. 264:7584-7589). Still alternatively, commercially available sources may be used, for example as sold by BD Biosciences, Gentest™, USA. P450 reductase may also be easily purified from animal (rat, mouse, rabbit) liver and liver microsomes, as described for example by French and Coon (1979) Arch. Biochem. Biophys. 195:565-577, and references therein.

A reaction volume contains CYP enzyme, P450 reductase, dilaurylphosphatidylcholine (DLPC), buffer solution and an excess of the reduced form of nicotinamide-adenine-dinucleotide phosphate (NADPH). Alternatively, a system regenerating NADPH in situ by an enzymatic reaction (glucose-6-phosphate dehydrogenase converts NADP+ to NADPH in the presence of the substrate glucose-6-phosphate) may be used. The reaction may be performed as described for CYP2A13 below.

In a particular embodiment, the human metabolic enzyme CYP2A13 is used.

The enzymatic reaction using CYP2A13 is performed as described below in the presence of potential substrates of the enzyme (test compounds) and in the presence of a reductase for CYP2A13.

An excess of human recombinant NADPH-P450 reductase contained in microsomes (may be purchased from Gentest, USA) is incubated with CYP2A13 enzyme in microsomes (enzymes are used for example in a ratio of 3:1 to 1:1, preferably 2.5:1 to 1.5:1, reductase to CYP2A13) for about 15 minutes on ice. CYP2A13 contained in microsomes corresponding to 1-200 pmoles, preferably 5-100 pmoles of the enzyme, is used per reaction.

Dilaurylphosphatidylcholine (DLPC, Fluka, Switzerland) is added from a freshly sonicated stock solution (1 mg/ml in water) to give a concentration of about 0.025 mg/ml in the final reaction volume and incubated on ice for about 15 minutes. A suitable reaction volume is 0.5 ml. In the case of coexpression of reductase and CYP enzymes in the same host cells, such as insect cells, yeast cells and bacterial cells, the step described above may be omitted, and the microsomes containing both enzymes may be used directly for incubation with test compounds in the presence of a suitable buffer. A suitable buffer, for example potassium phosphate, pH 7.4, is added with water to give a final buffer concentration of 0.1 M. The compounds to be tested (potential substrates for the CYP2A13 metabolic enzyme) are added, for example in a concentration of about 0.05 to 0.6 mM, preferably of about 0.2 to 0.5 mM. The enzymatic reaction is initiated by adding nicotinamide adenine dinucleotide phosphate (NADPH, Fluka, Switzerland). NADPH is preferably added in reduced form in water, for example about 0.01 to 0.05 ml, preferably 0.02 ml of a solution of 25 mM. The reaction is incubated for 10 to 120 min, preferably 30 to 90 min, most preferably 60 min at about 37° C. The duration of incubation may be adjusted depending on the sensitivity of the subsequent detection method used to identify test compounds (substrates) and the corresponding metabolites (products) of CYP2A13. The enzymatic reaction is stopped depending on the analysis method, as will be apparent to the skilled person, and the cell debris is separated by centrifugation. For example, addition of an organic acid such as trichloroacetic acid (e.g. in a final concentration of 5%), or addition of an organic solvent such as acetonitrile (e.g. in a final concentration of about 20-25%) lead to enzyme inactivation and mixtures are cooled on ice and precipitated proteins are removed by centrifugation.

If, for example, gas chromatography (GC) is used for analysis, extraction with an organic solvent such as methyl-t-butyl-ether (MTBE) separates substrates and products from the enzyme and no additional termination step is required. In this case, the samples are chilled on ice for 10 minutes, centrifuged and the supernatant is extracted with the organic solvent. The sample may then be analysed by chemical analytical methods, for example GC or GC linked to mass spectrometry (GC-MS). Alternatively, the aqueous phase may be analysed directly, i.e. without addition of organic solvent, for example by liquid chromatography (LC) or LC-MS is used as is apparent to the skilled person.

Metabolite formation may be optimized by the variation of the incubation conditions including concentrations for the CYP enzyme, P450 reductase, DLPC, NADPH, test compound concentrations, and incubation times according to the known practices of the art. A suitable substrate that may be used as a standard for optimization of an enzymatic reaction using CYP2A13 is coumarin, and the product of the enzymatic reaction, 7-hydroxy-coumarin (umbelliferone), can be easily monitored. Monitoring may be performed for example spectrofluorometrically, as described in the art at excitation wavelength of 368 nm and an emission wavelength of 456 nm. A preferred method of detecting umbelliferone is spectrofluorometrically monitoring at an excitation wavelength of 340 nm and an emission wavelength of 480 nm, which we find increases the detection sensitivity.

Metabolic methods according to the invention may be adapted depending on the type of compound that is to be identified, for example a substrate of a metabolic enzyme (precursor) and its metabolites, or a modulator of the enzyme such as an inhibitor or an activator of the metabolic enzyme.

Reaction with a Metabolic Enzyme: With Standard Substrate

In another embodiment, test compounds that influence the metabolism of flavour or fragrance compounds are identified in the metabolic method as described above by adding a known substrate as standard and detecting an occurring decrease or increase in the formation of the enzymatic reaction product of said standard. Compounds that influence the metabolism of flavour or fragrance compounds may be modulators of the enzyme (inhibitor, regulator or activator) or a competitive substrate of the enzyme.

The test compound, preferably in various concentrations, is incubated together with the metabolic enzyme and the standard substrate. The change of concentration of the standard or its enzymatic reaction product in the presence of a test compound as compared to the control reaction lacking the test compound is detected.

Test compounds or their metabolites of interest (competitive substrates, enzyme inhibitors, or positive or negative allosteric regulators of the enzyme) show a decrease or increase, when compared to a control reaction. The control reaction is lacking NADPH, which is an essential cofactor in CYP-catalysed reactions, during the reaction time, so that the enzymatic reaction cannot occur.

A decrease of the enzymatic reaction product of the standard substrate indicates that the test compound is a substrate of the enzymes and competes with the standard substrate, or the test compound is an inhibitor of the enzyme and decreases the turnover of substrate of the enzyme by binding competitively or non-competitively at the substrate binding site, or the test compound is a negative allosteric regulator and binding to the enzyme induces conformational changes which result in decreased enzymatic activity.

An increase of the enzymatic reaction product of the standard substrate indicates that the test compound is an allosteric activator that induces a conformational change of the enzyme upon binding resulting in an increased enzymatic activity.

Additionally, a chemical analysis on the absence or presence of metabolites and on their structure may be performed. Methods of chemical analysis are well known in the art and include GC and GC-MS.

The type of modulator of an enzyme may be further determined, for example as described below.

A compound is identified as a positive allosteric regulator of a metabolic enzyme by the occurrence of a dose-dependent increase of standard product formation when the concentration of the standard substrate is kept constant.

A compound is identified as an inhibitor or negative modulator by a decrease in the enzymatic reaction product of the standard substrate occurring in the absence of a metabolite of the compound. The presence or absence of a metabolite may be identified by chemical analytical methods as described herein-below.

In order to differentiate between a compound that is a competitive inhibitor or a negative allosteric regulator of the metabolic enzyme, such as a noncompetitive inhibitor, enzyme kinetic measurements may be employed as is well known in the art. These kinetic measurements allow to discriminate between reversible and irreversible inhibition. The kinetic properties of many enzymes may be described by the Michaelis-Menten model. When reaction velocities are plotted as a function of substrate concentrations and the plot, or the double-reciprocal plot, allow to determine substrate-specific kinetic constants for the enzyme (Michaelis constant and maximal velocity).

Reversible and irreversible inhibition may be distinguished as a result of the dissociation velocity of the enzyme-inhibitor complex, which is rapid in the case of the reversible inhibitor, and very slow in the case of the irreversible inhibitor which may be either covalently or noncovalently bound. Competitive and noncompetitive inhibition are distinguishable by the observed type of their enzyme kinetic.

The enzyme kinetic is plotted in double-reciprocal form for the enzymatic reaction using a standard substrate of the enzyme in the presence or absence of an inhibitor. A compound is identified as competitive inhibitor by an unaltered maximal velocity and an increased Michaelis constant of the enzyme in its presence. A compound is identified as a noncompetitive inhibitor by an unaltered Michaelis constant and a decreased maximal velocity of the enzyme in its presence.

A suitable standard substrate may be any known substrate that preferably is easily detected itself or produces easily detectable enzymatic reaction products.

Standard substrates that are fluorescent or form a fluorescent product, for example coumarin that forms umbelliferone, are preferred. Fluorescence measurements are highly sensitive and spectrofluometric measurements may be easily performed in single reaction containers as well as multiwell plates, for example containing 96, 384 or 1536 wells per plate.

In a particular embodiment, the metabolic enzyme CYP2A13 is used in the presence of a standard substrate.

The enzymatic reaction is performed as described above with the addition of a standard substrate to the reaction. A preferred standard substrate is coumarin, and its reaction product (umbelliferone) is easily detected by its fluorescence.

The test compounds are added, for example in a concentration of about 0.05 to 0.6 mM, preferably of about 0.1 to 0.3 mM, most preferably of about 0.2 mM. A suitable concentration of the standard substrate coumarin is about 0.01 to 0.25 mM, more preferably about 0.05 mM. The reaction volume may be any suitable volume, for example about 0.2 ml, which is a suitable volume to be handled in multiwell plates containing 96 reaction wells that may be used for fluorescent detection methods.

The enzymatic reaction is initiated by adding nicotinamide adenine dinucleotide phosphate (NADPH), and incubating for 10 to 120 min, preferably 30 to 90 min, most preferably 60 min at about 37° C. NADPH is preferably added in reduced form in water, for example about 0.01 to 0.04 ml, preferably 0.015 ml of a solution of 25 mM.

The enzymatic reaction may be stopped as described herein-above. For the controls, NADPH is added only after the stop of the enzymatic reactions to ensure correct fluorescent measurements. Alternatively, the control reaction may be immediately stopped after addition of NADPH to prevent any relevant enzymatic reaction taking place. Incubation conditions may be adjusted as described above.

Method of Identifying Compounds as Fragrance, Flavour or Modulator

In a method according to the invention, subsequent to the metabolic reaction a method of identifying a compound as a fragrance or flavour, or a modulator influencing the perception of such compounds, or their respective lead compounds, involving receptors for such compounds is performed. These receptor-based methods may comprise an in vitro receptor screening.

In Vitro Receptor Screen for Identifying Compounds as Fragrance, Flavour or Modulator Subsequent to a metabolic reaction as described above, an in vitro screening method using chemoreceptors may be performed with the test compound and their metabolites.

The sample resulting from the enzymatic reaction performed as described herein-above is centrifuged, the supernatant is diluted with 1 volume of 2×HEPES buffer, which may be used in the receptor screening method.

Depending on the enzyme and the buffer used, the cell system of the receptor screen of methods according to the invention will have to be adjusted, or in the alternative, when using a particular cell system, the enzyme buffer will have to be adjusted according to the tolerance of the cells for the enzyme buffer components, pH, and the medium they are cultured in. These adjustments can be performed according to methods well known in the art. To avoid negative effects on the cultured cells the probe containing enzyme and reaction products is centrifuged and the supernatant containing the reaction products is diluted with cell medium, preferably 1:1.

Preferred in vitro screening methods are employing olfactive receptors, taste receptors, pheromone receptors, or thermo receptors.

The screening method may be performed as known in the art, for example as described as described by Krautwurst et al. (1998) *Cell* 95:917-926; Haft et al. (1999) *Cell. Molec. Biol.* 45:285-291; Li et al. (2002) *PNAS* 99:4692-4696; Nelson et al. (2001) *Cell* 106:381-390; Chandrashekar et al. (2000) *Cell* 100:703-711; McKemy et al. (2002) *Nature* 416:52-58; Caterina et al. (1997) *Nature* 389:816-824.

Prior to performing a receptor screen, the receptor preferably is characterised and classified by its ligand(s) that may be compounds of known olfactive notes, or whose olfactive notes may be determined as described herein-below, for example by a human test subject. Such a classification may be, for example, green, fresh, woody, floral, fruity, animalic, spicy, gourmand, sweet, powdery and musk.

Depending on the nature of test compounds, the expected metabolites, and the type of fragrance/flavour or modulator that is to be identified, the following needs to be adapted as is apparent to the person skilled in the art: the choice of metabolic enzymes, the "composition" of the receptor screen, the "setup" of the "combined" screens the conditions for receptor screen, the prior characterisation of receptors of interest according to their ligands and their olfactive notes perceived.

In particular, a receptor screen may be used to identify agonists, antagonists and allosteric modulators among the test compounds i.e. the identified substrates and identified metabolites of the metabolic method performed.

In a particular aspect of the invention, inhibitors of enzymes are identified as intensifiers of receptor ligand properties by performing a metabolic method as described followed by an in vitro receptor screening method. For example, known agonists of receptors may be used as a standard when screening for modulating activity using odorant receptors. If no agonists are known, the screen with the respective odorant receptor may be performed to result in compounds that act as agonists. These may be used as such and then analysed by analytical methods.

If an enzyme substrate is an odorant test compound, and the metabolite is an odourless compound or a compound of less intensive odour than an odorant test compound itself, an inhibitor of the metabolic enzyme will result in a slower reaction of the metabolic enzyme with the odorant test compound and the concentration of a test compound that is a receptor agonist available to the receptor screen is higher and will accordingly result in a higher activation signal. These higher activation signals identify modulators that have a "boosting" effect (boosters), i.e. that intensify the overall odour or particular olfactive notes.

In a preferred embodiment, a receptor screen is performed after a metabolic reaction to identify boosters. For example, in case that the test compound is the agonist of a receptor (e.g. an odorant compound), that the test compound is metabolised, and that the resulting metabolite does not have the ability to activate the receptor (e.g. an odourless compound), a compound that would reduce, for example inhibit, the metabolic reaction would be a booster, resulting of the presence of a higher amount of the receptor activating or odorant compound. In another case, a test compound may not be able to activate a receptor (e.g. an odorless compound) but after occurance of a metabolic reaction its metabolite activates the receptor (e.g. an odorant compound which is formed from an odourless precursor). In the latter case, a booster for a compound with the mentioned characteristics would be a compound that increases the metabolic reaction.

In a particular embodiment, an enzyme is used to identify precursors for cooling compounds. For example, compound "A" is a precursor of a cooling compound "B". A is subjected to a metabolic reaction with one or more enzymes selected as disclosed herein. The metabolic reaction results in the formation of the cooling compound B that is responsible for a cooling sensation perceived in the human respiratory tract, particularly in the mouth. This is shown with a method according to the invention using as a test compound menthyl-lactate. As shown in example 7B, menthyl-lactate is metabolised by the esterase enzyme and the cooling compound menthol is formed. Menthol activates a cooling receptor in the subsequent receptor screen (compare example 8 and 9).

Receptors useful for methods according to the present invention belong to the superfamily of G-protein-coupled receptors or ion channels.

G-protein-coupled receptors (GPCRs) are integral membrane proteins characterized by amino acid sequences which contain seven hydrophobic domains, predicted to represent the trans-membrane spanning regions of the proteins. Some groups of GPCRs have been found to respond to odorants, tastants and/or pheromones.

One particularly useful group of GPCRs are olfactory receptors (ORs). ORs belong to the "Class A" of GPCRs. ORs are phylogenetically classified as Class I and Class II. For the mouse olfactory repertoire, a further classification was proposed with Class I ORs being given family numbers lower than 100 (1-42) (Zhang and Firestein (2002) *Nature Neuroscience*, 5:124-133). For the human olfactory subgenome, a classification in families and subfamilies has been proposed by Glusman et al. (2001) *Genome Research*, 11:685-702. From the 17 families, 13 belong to Class II, and 4 belong to Class I.

Alternatively, the human olfactory receptor genes have also been classified in 119 families, or 77 families if more than one genes has to be present in a family, by Zozulya et al. (2001) *Genome Biology* 2:0018.1-0018.12. Alternatively, the human olfactory receptor genes have also been classified in Class I and Class II, and Class II further divided in 19 Clades (A-S) based on phylogenetic analysis by Niimura and Nei (2003) *PNAS* 100:12235-12240.

All of the above-mentioned ORs may be successfully employed as receptors according to the present invention.

ORs couple to a heterotrimeric G-protein, which contains a specific G-alpha subunit (Golf) in olfactory sensory neurons, that activates an adenylate cyclases. Therefore, in a functional assay the presence of a G-Protein is needed. Other G-alpha proteins can be used, such G-alpha-16 as a promiscuous alternative, or chimeras of G-alpha proteins, and the signaling pathway may depend on the choice of the G-alpha protein. ORs may be employed in form of a functional assay as is well known in the art and described, for example, by Krautwurst et al. (1998) *Cell* 95:917-926; Hatt et al. (1999) *Cell. Molec. Biol.* 45:285-291; Spehr et al. (2003) *Science* 299:2054-2058; Kajiya et al. (2001) *J. Neurosci.* 21:6018-6025; Touhara et al. (1999) *PNAS* 96:4040-4045; Oka et al. (2004) *EMBO J.* 23:120-126.

A further group of GPCRs advantageously employed in the present invention are bitter taste receptors. These belong to the T2R family of GPCRs, are expressed in taste cells, and have been shown to respond to bitter compounds. T2Rs have a short extracellular amino terminus, and couple to a heterotrimeric G-protein, which contains a specific G-alpha subunit (gustducin), that activates a phosphodiesterase. Therefore, in a functional assay the presence of said G-protein, or a promiscuous alternative, such as for instance G-alpha-15 or G-alpha-16, or chimeras of G-alpha proteins, which are signaling via the inositol-1,4,5-triphosphate pathway, is needed (Lindemann (2001) *Nature*, 413:219)

Bitter taste receptors may be employed in form of a functional assay as is well known in the art and described, for example, by Chandrashekar et al. (2000) *Cell* 100:703-711; and Bufe et al. (2002) *Nat. Genet.* 32:397-401.

Still a further group of GPCRs advantageously employed in the present invention are sweet taste receptors, for example, T1R3 and T1R2 which need to be coexpressed to form a heterodimer. Said heterodimer forms the functional receptor for sweet stimuli. Sweet taste receptors may have large extracellular aminoterminal domains resembling the metabotropic glutamate receptors, as shown by T1R2 and T1R3. Sweet taste receptors may be employed in form of a functional assay as is well known in the art and described, for example, by Li et al. (2002) *PNAS* 99:4692-4696; and Nelson et al. (2001) *Cell* 106:381-390.

Another group of GPCRs advantageously employed in the present invention are umami receptors.

To the group of umami receptors belong the metabotropic glutamate receptor mGluR4 and in particular a taste-specific splice variant is involved in the perception of umami-like compounds which is described in the journal articles cited below. Metabotropic glutamate receptors belong to the "Class C" of GPCRs, having a large extracellular amino terminus.

Another receptor also belonging to the group of umami receptors responds to amino acids and in particular to glutamate, which is perceived to have an umami taste. The receptor is a heterodimer of T1R1 and T1R3, and the response is enhanced in the presence of purine 5'-ribonucleotides such as IMP and GMP which are known to pronounce the umami taste quality.

Umami receptors may be employed in form of a functional assay as is well known in the art and described, for example, by Li et al. (2002) *PNAS* 99:4692-4696; Chaudhari et al. (2000) *Nat. Neurosci.* 3:113-119; and Nelson et al. (2002) *Nature* 416:199-202.

Another group of GPCRs that may be employed in the present invention are human homologues of non-human pheromone receptors (putative pheromone receptors). In animals, pheromones are detected by the vomeronasal organ. It is still unclear whether there is a functional vomeronasal organ in human beings, and the fact that a VR-family member has been shown to be expressed in the main olfactory epithelium seems to indicate that human putative pheromone receptors may respond to odorants. Said odorants may or may not have pheromonal activities. Therefore, functionally, human pheromone-like receptors seem to be ORs, i.e. they bind a ligand which is an odorant and elicits a scent perception in humans, or otherwise influence scent perception. Like olfactory receptors, pheromone-like receptors may not only respond to odorants, but also to other volatile compounds, which may be odorless. In this case the activation of a receptor does not result in scent perception, but in another physiological effect, for example change in hormone release.

According to their expression in the vomeronasal organ of some non-human mammals, two families of vomeronasal receptors (VRs) have been classified: V1Rs and V2Rs. V1Rs have a short extracellular amino terminus like the ORs, and about 150 members have been identified in the mouse. V2Rs are similar to the metabotropic glutamate receptors, since they exhibit a large extracellular amino terminus, and the V2R family also consists of about 150 members.

In humans, VR-like genes have been identified that are expressed in the main olfactory epithelium (Rodriguez et al. (2000) *Nature Genetics*, 26:18-19. These genes may be cloned and the corresponding gene-products expressed by methods well known in the art, for example as described herein below.

Another superfamily of receptors that may be advantageously employed according to the present invention are Ion Channels. These include cooling receptors (also called thermoreceptors) and heat receptors (also called nociceptive receptors).

Cooling receptors are expressed by a particular subset of sensory neurons that contains thermoreceptors. Cooling receptors may belong to the Transient Receptor Potential family of channels (TRP), an example is TRPM8, which is activated by cold temperatures as well as by a cooling agent, for example menthol.

Cooling receptors may be employed in form of a functional assay as is well known in the art and described, for example, by Peier et al. (2002) *Cell* 108:705-715; McKerny et al. (2002) *Nature* 416:52-58; and Story et al. (2003) *Cell* 112:819-829.

Heat or nociceptive neurons are a particular subset of sensory neurons that contains thermoreceptors. Heat receptors may be members of the TRP family of channels. For example, the Vanilloid Receptor 1 (VR1), which is a member of the TRP family of channels, is activated by noxious heat.

Heat or nociceptive receptors may be employed in form of a functional assay as is well known in the art and described, for example, by Caterina et al. (1997) *Nature* 389:816-824; Grant et al. (2002) *J. Pharmacol. Exp. Therap.* 300:9-17; and Sprague et al. (2001) *Eur. J. Pharmacol.* 423:121-125.

Sensory Method of Identifying Test Compounds

Alternative or in addition to the in vitro screening method using receptors in vitro, a sensory method may be used to identify a compound useful as flavour/fragrance or modulator. Said sensory method includes gas chromatography-olfactometry ("GC-sniff") and olfactometer analysis.

GC-sniff

GC-sniff may be used to determine whether the metabolites generated in a metabolic reaction have an odour of interest. A human test subject, i.e. the receptor present in its native form in the human nose, is used as a detector to identify a compound as a flavour or fragrance.

In a preferred embodiment, the compounds are analysed by GC and "sniffed" simultaneously, i.e. olfactive properties of the compound are detected and described by a human test subject on a port at the same time when the compound is detected by the analytical tool and the compound is thereby identified as a fragrance or flavour. Metabolite(s) are extracted from the reaction mixture using an organic solvent such as MTBE as described above, and the MTBE fraction is used for GC analysis. The GC apparatus is equipped with a sniff port where part of the separated material is detected by the chemical detector of the apparatus and part of the material is directed to a glass funnel outside the device where the panelists can smell the compound and describe the olfactive properties of a metabolite.

Untrained human test subjects, for example 2-3, may be employed as panelists for a first identification of olfactive properties of a metabolite. Additionally, persons trained in sensory analysis are employed to characterise the olfactive qualities of the compounds of interest.

Olfactometer Analysis

In another aspect of the invention, olfactometers of the type as described in EP0883049 may be used to identify a test compound or metabolites, identified as receptor ligands by the in vitro screening method described above, as a modulator of the perception of flavour and fragrance compounds.

In another aspect of the invention, compounds identified as modulators of activities of metabolic enzymes which are present in the human nose, and identified modulators of olfactory receptor activities as described above are tested for their properties and activities when delivered to the human nose.

A panel of several human test subjects or panelists is employed. The olfactometer allows to adjust the concentration of a compound which a panelist is smelling at a glass funnel, by diluting a saturated vapour phase. Since panelist have different thresholds for a particular odorant, the threshold is determined for each panelist individually at the beginning of each experiment. Labelled magnitude scales (LMS) known in the art may be used. The LMS is a semantic scale of perceptual intensity characterised by a quasi-logarithmic scaling of its verbal labels, as described by Green et al. (1996) *Chemical Senses* 21:323-334. The positions of the verbal labels on the LMS, as percentage of full scale length, are: barely detectable, 1.4; weak, 6.1; moderate, 17.2; strong, 53.2; strongest imaginable, 100.

Two olfactometers may be used, and the compound of interest is present in one of the olfactometers, while a standard odor or odor mixture is present in both devices. For instance, the compound of interest is presented at different concentrations with a standard odor at invariant concentration. The panelist determines the presence of a difference between the presented stimuli, and describes the quantity and quality of the difference. Differences in olfactive properties between presented stimuli are described by panelists educated in sensory analysis or perfumers.

Alternatively, a single olfactometer may be used and the presented stimuli may be analysed by panelists serially.

Panelists are asked to determine the intensity of a known test odorant in the absence or presence of the compound to be identified, e.g. a potential modulator.

The olfactometer may be used to identify modulators of enzymatic activity or receptor susceptibility. Both the reference odorant (or odorant mixture) as well as the compound of interest (potential modulator) can be provided in a mixture at various concentrations and respective combinations, at random order during a session.

An odorant compound may be presented to panelists below, around and above their detection level (olfactory threshold).

Compounds are identified as inhibitors or negative allosteric regulators of metabolic enzymes by an increase in the intensity of perception of the test compound by the panelists occurring in the presence of the compound, provided that the metabolite has a decreased olfactory intensity, or is odorless. This increase may alter the quality of perception at higher concentrations.

In the case that both the test compound and its metabolite are odorants, the perceived olfative quality, if different, depends on the extent of enzymatic activity.

Positive allosteric regulators, and modulators of receptor susceptibility may be identified according to their performance.

Test compounds or metabolites can be antagonist or negative allosteric regulators of receptors responding to malodorants. Compounds that suppress or mask the perception of malodours are of interest in perfumery and may be identified by methods according to the invention as described hereinbelow.

Test compounds or their metabolites may be identified as modulators (for example boosters, masking agents) by the occurrence of the following effects:

After the metabolic reaction, test compounds or metabolites identified are compared by panelists to a control that contains the fragrance or flavour without the test compound or metabolite.

The test compounds and metabolites may be identified in mixtures containing several fragrance or flavour compounds to identify a boosting or masking effect.

A change in the overall intensity or quality of fragrance perception identifies a booster or a masking agent. A booster is identified by an increased overall intensity, a masking agent by a weaker overall intensity. Boosters or masking agents may boost or mask particular olfactive notes, such olfactive note specific boosters or masking agents are identified by the stronger or weaker perception of particular olfactive notes in a mixture.

Identified compounds may be used as lead structures for the identification of fragrances or flavours. The identified compounds may be odorants themselves, or they may modulate of the perception of flavours and fragrances without necessarily having an odour themselves.

Leads

After identifying a compound by a method according to the invention, a metabolic reaction and an in vitro receptor screen or a sensory method (GC-sniff, olfactometer analysis), the identified test compounds may be used as leads and derivatives may be synthesised in order to find flavour or fragrance compounds of particular desired qualities of interest. The derivatives are again used as test compounds in a method according to the invention as described hereinabove.

The procedure may be repeated until a compound of a particular desired olfactive note of interest, or a particular advantageous effect in combination with other flavour or fragrance compounds is identified. The compounds of interest can be flavour or fragrance compounds themselves, their metabolites or their precursors, compounds that improve the performance of flavour or fragrance compounds, or suppress or mask the perception of undesired olfactive notes of odorous compounds.

Analytical Methods of Analysing Compounds

Test compounds or metabolites of interest may be further analysed using analytical methods well known in the art, including GC, GC-MS, HPLC, HPLC-MS, and methods linked to GC and/or HPLC (LC).

In order to identify the structure of the compounds analytical databases may be consulted as is well known in the art. To compare e.g. GC retention time and MS pattern, the use of reference compounds are preferred.

Most preferably, metabolites are purified by a preparative method prior to employing an analytical method.

If the amount of material is limited to small quantities, preparative GC is preferred.

Purified compounds may be analysed by nuclear magnetic resonance ($^1$H-NMR and $^{13}$C-NMR) in order to elucidate their chemical structure.

Identification and Expression of Metabolic Enzymes

Applicant identified a large number of genes coding for metabolic enzymes which are expressed in the human olfactory mucosa. These include genes encoding epoxide hydrolases, esterases, flavin-containing monooxygenases, glutathione peroxidases, glutathione reductases, glutathione synthase, glutathione S-transferases, glutathione lyases, oxidases, peroxidases, epoxidases, reductases, rhodanese enzymes, sulfatases, sulfotransferases and UDP-glucuronosyltransferases and oxygenases.

The genes or their respective cDNA sequences corresponding to the metabolic enzymes identified as being expressed in the human olfactory mucosa are listed herein-above in Table 1.

Expression of the gene of a metabolic enzyme is a prerequisite for the synthesis and the presence of the protein. If the gene is expressed, the corresponding mRNA is present in the cell, and the occurrence of such mRNA species may be tested according to methods well known in the art. These include for example hybridising labelled probes originating from mRNA of a source of interest to DNA fixed on so-called GeneChips (DNA microarrays), and identification of specific mRNA species by conducting reverse-transcription polymerase chain reaction (RT-PCR) as described below.

Metabolic enzymes useful in the present invention may be those that are expressed in the cells of the oral cavity, the nasal cavity, and the respiratory tract. These include for example the epithelial cells lining the cavities and the glands of those areas. Of particular interest are metabolic enzymes expressed in the nasal mucosa, which contain the olfactory epithelium and neurons that express olfactory receptors.

The identification and expression of genes encoding metabolic enzymes is performed as described herein-below.

Identification of Genes of Metabolic Enzymes Expressed in the Olfactory Mucosa

The genes or their respective cDNA sequences corresponding to the metabolic enzymes identified as being expressed in the human olfactory mucosa are listed herein-above in Table 1.

By the methods used to identify and express these genes as described herein-below, further enzymes may be identified, and may be used in metabolic methods according to the invention as described herein.

Methods to identify gene expression in a given material are well known to the skilled person, and suitable methods may be found for example in Sambrook et al. 1989, "Molecular Cloning, A laboratory manual", Cold Spring Harbor Laboratory Press; and Ausubel et al. 1987, "Current Protocols in Molecular Biology", John Wiley & Sons, Inc.

A particularly useful method to identify a large number of probes is a global gene expression analysis on DNA microarrays.

Global Gene Expression Analysis on DNA Microarrays

A useful DNA microarray is the GeneChip® U95Av2 Array (Affymetrix, U.S.A.), that contains an extensive collection of human genes. Human adult and fetal tissues are used to prepare high quality RNA fractions. Total RNA may be prepared, for example, by using TRI Reagent (Molecular Research Centre, Cincinnati, Ohio). RNA fractions and total RNA may be purified, for example, using the RNeasy kit from Qiagen, Inc. (U.S.A.). Purified RNA is used to prepare double-stranded cDNA, which is used to synthesize cRNA labelled with biotin.

Labelled nucleic acid for gene microarray analysis from very small amounts of RNA using biotinylated nucleotides (such as Biotin-11-CTP, Biotin-16-UTP) may be performed by aRNA amplification, which is well known in the art and described for example in Baugh et al. (2001) *Nucleid Acids Res.* 29:E29; and Pabon et al. (2001) *Biotechniques* 31:874-879.

While other methods of nucleic acid amplification may be used for the analysis of global gene expression, aRNA amplification is preferred because the method does not significantly distort the relative abundance of individual mRNA sequences within an RNA population.

A suitable product to amplify and label RNA is MessageAmp™ aRNA, which may be purchased from Ambion (USA). The MessageAmp™ aRNA product (Ambion, USA) is based on an RNA amplification protocol that involves reverse transcription with an oligo(dT) primer with a T7 promoter and in vitro transcription of the resulting DNA with T7 RNA polymerase to generate hundreds to thousands of antisense RNA copies (aRNA) of each mRNA in a sample, as described by Gelder et al. (1990) *PNAS* 87:1663-1667.

A suitable DNA microarray is, for example, GeneChip® U95Av2 (Affymetrix, U.S.A.) Any suitable protocol for DNA microarray hybridization may be used, as will be apparent to the skilled person. For the U95Av2, a suitable protocol is outlined below. Prior to the hybridization, a portion of the labelled RNA sample is first hybridized to a Test chip, for example the Test3 chip (Affymetrix, U.S.A., "Test3") to determine RNA quality and labelling efficiency. As controls, two so-called housekeeping genes, actin (Accession No. X00351, National Centre for Biotechnology Information, NCBI), and GAPDH (Accession No. M33197, NCBI), are detected with probe sets hybridizing to the 5', middle, and the 3' region of the transcript. A small amount of four non-eukaryotic biotin-labelled RNA transcripts of known concentration is added to the labelled RNA samples as controls for proper hybridization and staining and detects the corresponding probe sets on the Test3. In a proper hybridization, the hybridization signals for the four transcripts should follow the same rank order as their relative abundance in the added control RNA.

RNA quality is checked with the Test3 as follows. RNA samples yielding a 3'/5' ratio of 1.5 or greater for the housekeeping genes are rejected, leaving the remaining "high quality" RNA. Preparation of fragmented biotin-labelled RNAs for hybridization to the U95Av2, the hybridization procedure itself, as well as the washing-staining-scanning procedure outlined below are described in the appropriate sections of a technical manual (GeneChip Expression Analysis, Technical Manual, 701021 Rev.4) available from the manufacturer (Affimetrix, USA).

The U95Av2 is subsequently washed and stained with streptavidin phycoerythrin (SA-PE) using a fluidics station, and subsequently placed into an argon-ion laser scanner which excites fluorescently labelled targets and collects emitted energy into a fluorescent image. The presence or absence of individual transcripts may be determined as well known to the skilled person, for example using MicroArray Suite software (version 4.0, Scanalytics, USA.), which is supplied with the Affimetrix (USA), GeneChip® System Gene Array scanner, GeneChip® Fluidics stations, GeneChip® Workstation system, GeneChip® hybridization oven (all by Agilent Technologies, USA).

The transcripts of metabolic enzymes in the human nasal mucosa are identified using U95Av2 as described and are included in Table 1 above. Results with U95Av2 may be confirmed with RT-PCR using specific oligonucleotide primer to amplify specific gene sequences that originate from transcripts present in cells of the tissue of the olfactory mucosa. A strong positive correlation between results generated with biotin-labelled probes originating from adult versus fetal RNA samples is observed.

RT-PCR

Alternatively to the global gene expression analysis, expression may be analysed or, after hybridization to DNA microarrays, further confirmed, by RT-PCR and/or real-time quantitative RT-PCR, as is apparent to the skilled person.

Metabolic Enzymes: Cloning, Expression, Purification and Identification

The genes of metabolic enzymes may be cloned, expressed in suitable host cells, and the corresponding recombinant protein (the metabolic enzyme) may be expressed in and isolated from said host cells according to methods well known in the art, for example as described below.

RNA isolated from human olfactory mucosa is reverse transcribed and suitable primers are designed which are specific to the metabolic enzyme gene for amplification of the full-length cDNA clone by polymerase-chain reaction (PCR). Alternatively, RNA from other tissues more readily obtained in sufficient quantity or quality, for example liver, may be used.

The PCR-product is purified and cloned in a vector with a suitable multiple cloning site, for example pGEM-T (Promega Corp., U.S.A.). The nucleotide sequence of the metabolic enzyme gene is confirmed by DNA sequencing. The methods of reverse transcription, primer selection, PCR amplification, PCR-product purification, cloning of a PCR-product and DNA sequencing are well known to the skilled person and described for example in Sambrook et al. (1989) "Molecular Cloning, A laboratory manual", Cold Spring Harbor Laboratory Press.; and Ausubel et al. (1987) "Current Protocols in Molecular Biology", John Wiley & Sons, Inc.

A gene of a metabolic enzyme may be heterologously expressed in any suitable host cell, for example in *Escherichia coli*, yeast, mammalian cells and insect cells, as will be apparent to the skilled person, for example as described for human CYP genes by Lee et al. (1996) *Meth. Enzymol.* 272: 86-95 and references therein.

Expression of the gene and production of the corresponding protein may be performed, for example, in insect cells. Suitable insect cells are for example Sf9 cells (Invitrogen Corp., U.S.A., American Type Culture Collection (ATCC) No. CRL-1711). For production in insect cells, the gene may be cloned, for example, in the baculovirus vector pBlueBac4.5 (Invitrogen Corp., U.S.A.).

The procedures may be performed as well known in the art, for example as described in the following references: Kitts and Possee (1993) *BioTechniques* 14:810-817; King and Possee (1992) "The Baculovirus Expression System: A laboratory guide", Chapman and Hall, New York, U.S.; O'Reilly et al. (1992) "Baculovirus Expression Vectors: A laboratory manual", W.H. Freeman and Company, New York, U.S.; Richardson (Walker, Ed.) (1995) "Baculovirus Expression Protocols", Methods in Molecular Biology, Vol. 39, Humana Press, Totowa, U.S.A.

The production of the recombinant baculovirus may be carried out, for example, as outlined below. Sf9 cells are cotransfected with the recombinant metabolic enzyme gene containing vector, pBlueBac4.5 vector, together with linearised Bac-N-Blue DNA, which contains essential viral DNA sequences.

Successful recombination of the engineered pBlueBac4.5 and Bac-N-Blue DNA results in the formation of a full-length beta-galactosidase (lacZ) gene and allows identifying the recombinant viruses as blue plaques in the presence of the chromogenic substrate X-gal (5-bromo-4-chloro-3-indolyl-beta-D-galactopyranoside), which is used in conjunction with IPTG (Isopropyl-beta-D-Thiogalactopyranoside) to detect beta-galactosidase activity (Kitts and Possee (1993) *BioTechniques* 14:810-817). Single plaques are isolated and recombinant viruses propagated and analysed by PCR. Several stages of virus amplification may be required to obtain a high-titer and large-volume virus stock, which is used for Sf9-cell infection and enzyme production.

Insect cells may be cultured and infected with baculovirus, for example, as described below.

For infection, the virus may be used at multiplicity of infection (MOI) levels of 0.01 to 10, suitably between MOI 0.5-5 with cells of a density of $1.0-2.5 \times 10^6$ per ml, for example between 1.5 and $2.0 \times 10^6$ cells per ml. Cells are cultured in flasks and spinners slightly above or around room-temperature, usually at 27° C. in an incubation hood in a suitable medium known to the skilled person. Cells are infected by adding the virus in the amount indicated above with MOI levels between 0.01 and 10. The optimal yield and specific activity of the protein of interest may be identified by testing several MOI levels.

The expression level or concentration and yield of the produced protein may be determined using antibodies raised against the protein following immuno blotting or Western blotting protocols which are well known in the art, and described for instance in: Sambrook et al. (1989) "Molecular Cloning, A laboratory manual", Cold spring Harbor Laboratory Press; and Ausubel et al. (1987) "Current Protocols in Molecular Biology", John Wiley & Sons, Inc.

The activity of the produced metabolic enzyme is tested by an enzymatic assay. The assay characteristics vary with the particular enzyme used and factors that need to be adjusted accordingly include buffer solutions, cofactors, pH, salt concentrations, temperature, and substrates, as will be apparent to the skilled person.

Enzymatic reactions conditions for metabolic enzymes listed in Table 1 and Table 2 are known in the art. The enzymatic assay for CYP2A13 is performed as described herein above using as a standard substrate, for example coumarin, instead of the test compound.

For CYP enzymes, which contain a heme cofactor, cultures are supplemented with hemin (a final concentration of about 0.001-0.005 mg/ml), about 24 hours after addition of the recombinant baculovirus, and incubated for another 48 hours in spinner flasks. Instead of hemin (for example hemin chloride or hemin arginate), other heme supplements may be added to the culture medium, for example heme precursors including 5-aminolevulinic acid and iron citrate.

Values of MOI, hemin concentration, cell density and incubation times may have to be adjusted for optimal results, as will be apparent to the skilled person and is described, for example, in Phillips and Shephard (1998) "*Methods in Molecular Biology*, Vol. 107: *Cytochrome P450 Protocols*", Humana Press, Totowa, N.J.; and Johnson and Waterman (1996) "*Methods in Enzymology*, Vol. 272: *Cytochrome P450 (Part B)*", Academic Press, San Diego, Calif.

The expression of membrane-bound proteins and their purification is well known to the skilled person. Membrane-bound proteins such as CYP enzymes may be prepared from microsomes, for example, as described in Zhang et al. (1997) *Arch. Biochem. Biophys.* 340:270-278. Alternatively, cell lysis may be performed by sonification or homogenization using a polytron mixer or a combination of the two. Resuspended microsomes are used to determine the CYP carbon monoxide (CO) spectrum to determine the concentration of CYP contained per ml of preparation, as described by Omura and Sato (1964) *J. Biol. Chem.* 239:2370-2378.

Enzymatic activity is confirmed in an enzymatic assay, for example as described herein above by adding a test substrate which produces an easily analyzable metabolite, such as the substrate coumarin that will form as its metabolite 7-hydroxy-coumarin (umbelliferone) upon hydroxylation by the metabolic enzyme CYP2A13.

Microsomes containing the CYP protein and microsomes containing the P450 reductase are combined for the metabolic reaction using CYP enzymes as described herein above. Alternatively, Sf9 cells can be co-infected with recombinant baculoviruses for CYP protein and P450 reductase to produce membranes containing both enzymes.

This has the advantage of the enzymes having close physical proximity which is advantageous for catalytic activity. For co-infection, optimal ratios of the two viruses used and enzymatic activity in the microsomal preparation is determined as is apparent to the skilled person.

If the CYP microsomes are combined with separate P450 reductase microsomes, the latter may be produced in Sf9 using a recombinant baculovirus as described above, or may be purchased, for example, from Gentest (BD Biosciences, Gentest™, U.S.). Alternatively, microsomes containing P450 reductase may be produced in *Escherichia coli* as described in Shen et al. (1989) *J. Biol. Chem.* 264:7584-7589.

Metabolic Method Employing Polymorphisms

Genes may be different among individuals (genetic polymorphisms, for example single nucleotide polymorphisms ("SNPs")) and small variations in genes for metabolic enzymes may have significant consequences on activities and properties of the corresponding enzyme.

For metabolic enzymes which are expressed in the nasal mucosa these may include differences in flavour and fragrance compound metabolism, and differences in the perception of flavours and fragrances.

The identification of genetic polymorphisms, for example SNPs, will be apparent to the skilled person and may be performed by amplifying and sequencing the chromosomal region harbouring the structural gene of interest, for example as described in Zhang et al. (2002) *Journal of Pharmacology and Exp. Therapeutics,* 302:416-423, Nagata and Yamazoe (2002) *Drug Metabol. Pharamacokin.* 17:167-198; Roden and George (2002) *Nature Reviews Drug Discovery*, 1:37-44.

For the metabolic enzyme CYP2A13, useful genetically polymorphic variants of the gene are listed in Table 3. These and further variants have been described in Zhang et al. (2002) *Journal of Pharmacology and Exp. Therapeutics*, 302: 416-423.

The identified variants of the gene of the metabolic enzyme of interest may be used to clone, express and purify the corresponding metabolic enzyme variant as described herein-above. Said metabolic enzyme variant may then be used in a metabolic method as described herein-above.

In another aspect, the invention therefore provides a method to identify fragrances and flavours as described herein-above for the metabolic enzyme CYP2A13, comprising multiple polymorphic versions of one or more metabolic enzyme.

For methods according to the invention as described herein-above, purification procedures and analytical methods for metabolites may be adjusted depending on the enzymes and substrates used, and depending on the resulting products, as will be immediately apparent to the skilled person.

For example, the type of organic solvents used during extraction and different analytical parameters including the wavelengths for spectrophotometric and/or spectrofluorometric analysis may have to be adjusted.

Likewise the scale of reactions may be adjusted. A suitable scale may be in microtiter plates, for example having a format of 96-, 384- or 1536-wells. These formats are particularly useful to run series of reactions in parallel.

Instead of fragrance or flavour compounds, the metabolic method according to the invention may be used to identify other compounds which are bound by receptors located in the olfactory epithelium or epithelium of the mouth. For example, the metabolic method may be used to identify pheromones and ligands of thermo receptors. As apparent to the skilled person, the in vitro receptor screen or sensory methods will have to be adjusted depending on the nature of the compound be identified, as will be apparent to the skilled person.

EXAMPLES

Example 1

Cloning and Expression of the Gene Encoding Human CYP2A13, and Production and Isolation of CYP2A13 Microsomes Total RNA is isolated from human olfactory epithelium using the RNeasy midi Kit (Qiagen, Germany). The isolated RNA is reverse transcribed using Superscript II (MMLV) Reverse Transcriptase (Gibco, USA). The reaction is performed using 19.5 ng poly(A)mRNA and an oligo(dT) primer in a total volume of 20 µl, resulting in a cDNA product.

The cDNA product is amplified four times by polymerase-chain reaction (PCR) using primers specific to the CYP2A13 gene at an extension temperature of 72° C. in a volume of 25 µl as follows. In the first PCR reaction 1 µl reaction volume with cDNA is used with primer No. 1 (5'-ATATCCTTAGGC-GACTGAGG-3') (5'2A13) and primer No. 2 (5'-CAGGGCT-GCTTCTGGTGA-3') (3'2A13ext) at an annealing temperature of 67° C. for 35 cycles. A second nested PCR reaction is performed using 1 µl reaction volume of the product of the first PCR reaction and primer No. 3 (5'-ATATCCTTAGGC-GACTGAGG-3') (5'2A13) and primer No. 4 (5'-GTCT-TGATGTCAGTCTGGCG-3') (3'2A13int), at an annealing temperature of 65° C. for 30 cycles. A third PCR reaction is performed for extension using 1 µl reaction volume of the product of the second PCR reaction and primer No. 5 (5'-TCTGGTGACCTTGCTGGCCTGCCTGACT-GTGATGGTCTTGATGTCTGTTTGG-3') (CYP-1-2F) and primer No. 6 (5'-GGGATCGTGGCAAAGCCCACGT-GTTTGGGGGACACGTCAATGTCCTTAG- GCGACTGAGGA-3') (CYP-5-3R/1) at an annealing temperature of 62° C. for 35 cycles. A fourth PCR is performed for extension using 1 µl reaction volume of the product of the third PCR reaction and primer No. 7 (5'-TATGAATTCTAT-GCTGGCCTCAGGGCTGCTTCTGGTGACCTTGC-TGGCCT-3') (CYP-1-3F) and primer No. 8 (5'-AGAAGCT-TATCAGCGGGGCAGGAAGCTCATGGTG-TAGTTTCGTGGGATCGTGGCAAAGCCCA-3') (CYP-5-4R) at an annealing temperature of 62° C. for 35 cycles. Primer No. 7 contains a recognition site for the restriction enzyme EcoRI, primer No. 8 contains a recognition site for the restriction enzyme HindIII. The product of the fourth PCR reaction spans the entire open reading frame of the CYP2A13 gene, which is flanked by the restriction enzyme recognition sites for EcoRI and HindIII.

Said product of the fourth PCR is digested with EcoRI and HindIII restriction enzymes to result in a DNA fragment that includes the entire open reading frame. Said DNA fragment is purified using the QIAquick PCR Purification Kit columns (Qiagen, Germany) and cloned in the cloning vector pGEM-T (Promega Corp., USA).

The nucleotide sequence of the cloned DNA fragment is compared with the known cDNA sequence for CYP2A13 (GenBank accession No. AF209774). Several clones are sequenced and shown to have single base pair variations due to sequence errors occurring during PCR. By comparing to the known sequence, correct fragments of several clones are chosen, combined and subcloned in the cloning vector pUC19 using EcoRI and HindIII in the multiple cloning site to give the correct complete sequence. The recombinant pUC19 vector containing the cDNA of CYP2A13 is digested with EcoRI and HindIII and the DNA insert containing the CYP2A13 cDNA sequence is ligated into the expression vector pBlueBac4.5 (Invitrogen Corp., USA) to give a recombinant baculovirus expression vector.

Sf9 insect cells are cotransfected with the recombinant pBlueBac4.5 vector containing CYP2A13 cDNA together with linearised Bac-N-Blue DNA (Invitrogen Corp., USA) which contains essential viral DNA sequences to produce the recombinant baculovirus. To prepare the transfection mixture in a 1.5 ml microcentrifuge tube, 10 µl (0.5 µg) of Bac-N-Blue DNA are combined with 4 µl of the recombinant plasmid (1 µg/µl) and 1 ml of Grace's Insect Media (without supplements or fetal bovine serum; Invitrogen Inc., USA) and 20 µl of InsectinPlus Liposomes (Invitrogen, Inc., USA). The transfection mixture is vigorously vortexed for 10 seconds, and incubated at room temperature for 15 minutes. For transfection, $2 \times 10^6$ log phase Sf9 cells are seeded in a 60 mm dish and allowed to fully attach for 25 minutes. The medium is carefully removed before adding the transfection mixture dropwise to the cells in the 60 mm dish. The dishes are incubated at room temperature for 4 hours on a side-to-side, rocking platform with a low speed adjusted to about 2 side-to-side motions per minute. Following the 4-hour incubation period, 1 ml of TNM-FH medium (Invitrogen, Inc.) is added to the 60 mm dish, the dish placed in a sealed plastic bag and incubated at 27° C. Transfection of the recombinant pBlue-Bac4.5 and Bac-N-Blue DNA results in the formation of a full-length beta-galactosidase (lacZ) gene and recombinant viruses containing the CYP2A13 cDNA are identified as blue plaques in the presence of the chromogenic substrate X-gal. Recombinant viruses from single plaques are isolated, propagated and analyzed by PCR using primers No. 1 and No. 2. Propagation of the recombinant virus is performed by several consecutive cell infections until a high-titer ($2 \times 10^8$ PFU/ml) large-volume virus stock is obtained.

Cells are cultured in spinners at about 27° C. in an incubator. For infection, a multiplicity of infection (MOI) of 2 is used. Following infection, cultures are supplemented with hemin (final concentration between 0.003 mg/ml) 24 hours after addition of the recombinant baculovirus, and cultures are incubated for another 48 hours in spinner flasks. Microsomes containing CYP enzyme are prepared and purified as described in Zhang et al. (1997) *Arch. Biochem. Biophys.*, 340:270-278. Resuspended microsomes are used to determine the CYP carbon monoxide (CO) spectrum to determine the concentration of CYP contained per ml of preparation, as described by Omura and Sato (1964) *J. Biol. Chem.* 239:2370-2378.

Example 2A

Incubation of a Test Compound with Human CYP2A13 and Identification of Metabolites A test compound (potential substrate of CYP2A13) is incubated with CYP2A13 in the presence of a cytochrome P450 reductase. CYP2A13 is employed in form of microsomes which are prepared as described in Example 1. 100 pmoles human recombinant NADPH-P450 reductase contained in microsomes (BD Biosciences Gentest, USA) are incubated with 50 pmoles CYP2A13 microsomes for 15 minutes on ice. Freshly sonicated dilaurylphosphatidylcholine (DLPC, Fluka, Switzerland) is added from a stock solution (1 mg/ml in water) to give a final concentration of 0.025 mg/ml (0.5 ml final reaction volume) and the mixture is incubated on ice for 15 minutes. Potassium phosphate buffer (1 M, pH 7.4) and water are added to give a buffer concentration of 0.1M in a final volume of 0.5 ml. The test compound is prepared as a 50 mM stock solution in acetonitrile. The test compound is added from the stock to give a final concentration of 0.3 mM. For each test compound two samples are prepared, one sample being the negative control where no enzymatic reaction occurs. To one sample, 0.02 ml of a solution of 50 mM nicotinamide-adenine-dinucleotide phosphate (NADPH, Fluka, Switzerland) in water is added to initiate the enzymatic reaction. To the second sample (control), 0.02 ml of water is added instead of NADPH. The samples are incubated for 60 min at 37° C.

Following the 60 min incubation, the sample is chilled on ice for 10 minutes and the enzymatic reaction is stopped by extraction with 0.3 ml of the organic solvent methyl-t-butyl-ether (MTBE) that allows separating the test compound and its metabolites from the aqueous phase which contains the enzymes. 1 microliter of the MTBE fraction is analysed by GC and GC-MS to identify metabolites which are present in the enzymatic reaction, but not in the control.

Example 2B

Incubation of 2-Methoxyacetophenone with Human CYP2A13 and Identification of Metabolites The procedure as described in Example 2A is followed using 2-methoxyacetophenone (Fluka, Switzerland) as test compound. A stock solution of 50 mM is prepared in acetonitrile. The samples contain 0.3 mM 2-methoxyacetophenone. GC-analysis of the samples after their incubation with the enzyme shows that an additional peak with a retention time different from the test compound is present in the sample, but not in the control. GC-MS analysis identifies this peak as 2-hydroxyacetophenone. This result is confirmed by analysing a reference sample of 2-hydroxyacetophenone (Fluka, Switzerland) by GC and GC-MS.

Example 3A

Incubation of a Test Compound with Human CYP2A13 and a Standard Substrate, and Identification as Substrate or Modulator The incubation of a test compound and an enzyme is performed as described for Example 2A subject to the following modifications: The final concentration of the test compound is 0.2 mM. As standard substrate coumarin is used at a final concentration of 0.05 mM. The final total volume is 0.25 ml, which is suitable for microtiter plates. The enzymatic reaction is initiated by the addition of 0.01 ml of a solution of 50 mM NADPH in water. The samples are incubated for 60 min at 37° C. After 60 min, the enzymatic reaction is stopped by the addition of 0.02 ml cold 50% trichloroacetic acid (TCA) and incubated at 4° C. for 15 min. 0.01 ml of a solution of 50 mM NADPH in water is added to the control. Denatured proteins and other unsoluble parts are separated by centrifugation (10 min., 560×g, at room temperature).

The samples are analysed spectrofluorometrically which allows to detect the formation of umbelliferone as the enzymatic product from the standard substrate coumarin at an excitation wavelength of 340 nm and an emission wavelength of 480 nm. A change of the fluorescent signal at 480 nm with respect to the control (increase or decrease) shows that the test compound or its metabolite is influencing enzymatic activity or the formation of the product of the standard substrate (the test compound is a substrate or a modulator).

For test compounds which show a decrease in umbelliferone-derived fluorescence, the incubation with the enzyme but without coumarin and analysis of metabolites is performed by GC and GC-MS as described in Example 2A. The identification of additional peaks in comparison to the negative control indicates the formation of metabolites of the test compound. Metabolites are identified by GC-MS. The identification of one or more metabolites shows that the test compound is a substrate of CYP2A13.

A decrease in umbelliferone-derived fluorescence after incubation in presence with coumarin and a lack of additional peaks in GC and GC-MS analysis shows that the test compounds is a negative modulator (inhibitor or negative allosteric regulator) of CYP2A13 activity.

For test compounds resulting in an increase of fluorescence, at least one of the test compound or its metabolite(s) is a positive modulator (positive allosteric regulator) of enzymatic activity. If there are no metabolites, as is shown by a lack of additional peaks in GC and GC-MS, the test compound is a positive allosteric regulator of CYP2A13 activity.

The identification of the metabolites is performed by analysis of their structure. The structure is elucidated by the MS pattern of the corresponding peak and comparison to MS databases. Alternatively, the metabolite is isolated and the structure is elucidated by NMR.

The metabolite(s) that are identified can be either isolated, purchased or synthesised. The metabolites are analysed as described above for the original test compounds to determine whether the modulating effect is based on these metabolites themselves.

An identified modulator is further confirmed as follows. The modulator is treated as described for a test compound above with the following modifications: 2-methoxyacetophenone is used as standard substrate, which is reacting enzymatically to 2-hydroxyacetophenone.

The concentration of the standard substrate 2-methoxyacetophenone is 0.05 mM. Several samples of the modulator are prepared at various concentrations, for example 0, 0.01, 0.02, 0.05, 0.1, 0.2 and 0.5 mM. The reactions are performed for example in 1.5-ml reaction tubes at a volume of 0.5 ml. The reactions are stopped and extracted as described in Example 2A, and 1 microliter of MTBE is analysed by GC and GC-MS.

The modulating activity of the modulator is confirmed by the occurrence of a dose-dependent enzymatic reaction dependent on the concentration of the modulator.

An identified negative or positive modulator (inhibitor, negative allosteric regulator, positive allosteric regulator) is further confirmed as follows.

The modulator is treated as described above with the following modifications. The concentration of coumarin is 0.05 mM. Several samples of the modulator are prepared at various concentrations, for example 0, 0.01, 0.02, 0.05, 0.1, 0.2 and 0.5 mM. The final total volume is 0.25 ml, which is suitable for microtiter plates. The enzymatic reaction is initiated by the addition of 0.010 ml of a solution of 50 mM NADPH in water. The samples are incubated for 60 min at 37° C. After 60 min, the enzymatic reaction is stopped by the addition of 0.02 ml cold 50% trichloroacetic acid (TCA) and incubated at 4° C. for 15 min. 0.010 ml of a solution of 50 mM NADPH in water is added to the control. Denatured proteins and other unsoluble parts are separated by centrifugation (10 min, 560×g, room-temperature).

The samples are analysed spectrofluorometrically which allows to detect the formation of umbelliferone as the enzymatic product of coumarin at an excitation wavelength of 340 nm and an emission wavelength of 480 nm. A decrease of the fluorescent signal at 480 nm with respect to the control shows that the test compound is influencing enzymatic activity and confirms the nature of an inhibitor, since no metabolites have been detected.

Example 3B

Incubation of N,N-Dimethylaniline with Human CYP2A13 and Coumarin, and Identification as Substrate N,N-dimethylaniline is used as test compound as described in Example 3A. A decrease in the formation of umbelliferone is detected when compared to the negative control. GC and GC-MS analysis show the formation of an additional peak which is identified as N-methylaniline, which is a metabolite of N,N-dimethylaniline. Accordingly N,N-dimethylaniline is identified as a substrate of CYP2A13.

Example 4

Identification of CYP2E1 Gene Expression in Human Olfactory Mucosa by RT-PCR

RNA is isolated, reverse transcribed and cDNA prepared as described in Example 1.

The cDNA product is amplified by polymerase-chain reaction (PCR) using primers specific to an internal region of the CYP2E1 gene. 1 µl of cDNA is used with primer No. 9 and primer No. 10 at an annealing temperature of 55° C. and an extension temperature of 72° C. for 50 cycles in a reaction volume of 25 µl. 1 µl of the PCR product is used for a nested PCR using primer No. 11 (5'-CTACAAGGACGAGTTCTC-3') (CYP2E1-5-int) and primer No. 12 (5'-GAGTTGGCAC-TACGACTG-3') (CYP2E1-3-int) at an annealing temperature of 55° C. and an extension temperature of 72° C. for 30 cycles in a reaction volume of 25 µl. Analysis of the PCR product from the second, nested PCR by agarose gel electrophoresis shows a single DNA band of the expected size, which confirms that the CYP2E1 gene is expressed in the human olfactory mucosa.

Example 5

Cloning and Expression of the Gene Encoding CYP2E1, and Production and Isolation of CYP2E1 Microsomes For cloning of the full-length gene encoding CYP2E1, a commercially available human liver cDNA library (BD Biosciences Clontech, USA) is used as template in a PCR reaction. Primers are chosen to bind to the ends of the coding sequence to amplify the sequence in between.

A PCR reaction is performed using 0.2 µl of the liver cDNA library in a reaction volume of 25 µl, using primer Seq No. 9 (5'-GATGTCTGCCCTCGGAGTG-3') (CYP2E1-5-full) and primer Seq No. 10 (5'-CTCATGAGCGGGGAATGAC-3') (CYP2E1-3-full), at an annealing temperature of 55° C., and an extension temperature of 72° C. for 35 cycles. The reaction product is purified using the QIAquick PCR Purification Kit columns (Qiagen, Germany) and cloned in the cloning vector pGEM-T-Easy (Promega Corp., USA). From several plasmids, the sequence of the insert containing the known CYP2E1 coding sequence is confirmed by DNA sequencing. A recombinant clone with a correct CYP2E1 coding sequence corresponding to GeneBank accession No. J02843 is selected and digested with EcoRI, and the DNA insert containing the CYP2E1 cDNA sequence is ligated into the expression vector pBlueBac4.5 (Invitrogen Corp., USA) and the correct orientation confirmed to give a recombinant baculovirus expression vector. Production of recombinant viruses, insect cell infection and preparation of CYP2E1-containing microsomes are performed as described in Example 1, using the primers No. 9 and 10 indicated above to analyse recombinant viruses from single isolated plaques.

Example 6

Cloning and Expression of the Gene Encoding Human Carboxyl Esterase (CE), and Production and Isolation of CE Microsomes Expression of the human carboxyl esterase gene (CE, GeneBank Accession No. L07765) in olfactory mucosa is confirmed by a positive signal in the Gene Array analysis as described in this invention (see Table 1). In order to clone the full-length gene encoding CE, a commercially available liver cDNA library (BD Biosciences Clontech, USA) is used as template, and primers designed to the ends of the coding sequence. A PCR reaction is performed using 0.2 µl of the liver cDNA library in a reaction volume of 25 µl, using primer Seq No. 13 (5'-GATGTGGCTCCGTGCCTTTATC-3') (CE-5-full) and primer Seq No. 14 (5'-CTTCATTCACAGCTC-TATGTGTTC-3') (CE-3-full), at an annealing temperature of 55° C., and an extension temperature of 72° C. for 30 cycles. The reaction product is purified using the QIAquick PCR Purification Kit columns (Qiagen, Germany) and cloned in the cloning vector pGEM-T-Easy (Promega Corp., USA). From several plasmids, the sequence of the insert containing the known CE coding sequence is confirmed by DNA sequencing. A recombinant clone with correct CE sequence is selected and digested with EcoRI, and the DNA insert containing the CE cDNA sequence is ligated into the expression vector pBlueBac4.5 (Invitrogen Corp., USA) and the correct orientation confirmed to give a recombinant baculovirus expression vector. Production of recombinant viruses, insect cell infection and preparation of CE-containing microsomes are done as described for CYP in Example 1 using the primers indicated above to analyse recombinant viruses from single isolated plaques except that the addition of hemin is omitted, since CE does not contain this cofactor.

Example 7A

Incubation of a Test Compound with Human Recombinant Carboxyl Esterase (CE) and Standard Substrate p-Nitrophenylacetate, and Identification as Substrate or Modulator The incubation of a test compound (potential substrate or modulator of CE) and CE is performed in the presence of a standard substrate, for example p-nitrophenylacetate. The hydrolysis product of p-nitrophenylacetate is p-nitrophenol which can be detected by measuring the absorbance at 405 nm. CE is employed in the form of microsomes which are prepared as described in example 6.

The incubation mixture contains CE microsomes containing CE enzyme corresponding to 4 mU of CE in a total volume of 0.2 ml (1 U hydrolyzes 1.0 µmole of ethylbutyrate to butyrate and ethanol per min at pH 8.0, 25° C.), 0.1 mM p-nitrophenylacetate, and the test compound in 50 mM potassium phosphate buffer (pH 7.2). The test compound is employed at different concentrations, for example 0, 0.05, 0.1, 0.25, 0.5, 1 mM, to allow detection of a dose-dependent effect. Samples that contain no test compound serve as a negative control. The samples are incubated at 25° C. and the increase in absorbance at 405 nm is measured every 5 minutes for 30 minutes.

A reduced formation of p-nitrophenol and accordingly reduced absorbance in samples containing the test compound compared to negative controls indicates the presence of either a competitive substrate or a negative modulator (an inhibitor or negative allosteric regulator). An increase in absorbance indicates the presence of a positive allosteric regulator of CE. The further identification and confirmation of compounds and/or metabolites may be performed analogous to the method described in example 3A using GC and GC-MS to analyse the assay results in the absence of the standard substrate p-nitrophenylacetate.

Example 7B

Incubation of Menthyl-lactate with Human Recombinant Carboxyl Esterase (CE) and Standard Substrate p-Nitrophenylacetate, and Identification as Substrate or Modulator Menthyl-lactate is used as test compound as described in Example 7A. A concentration-dependent decrease in the formation of the enzymatic reaction product of p-nitrophenylacetate is detected when compared to the negative control.

Incubation with CE is performed in the absence of the standard substrate using 10 mU of CE in a total volume of 0.5 ml with the substrate at 0.25 mM and 50 mM potassium phosphate as the assay buffer. After 30 min incubation time at 25° C., the samples are extracted with MTBE and analysed by GC and GC-MS.

GC and GC-MS analysis show the formation of an additional peak which is identified as menthol, which is a metabolite of menthyl-lactate. Accordingly menthyl-lactate is identified as a substrate of human CE.

Example 8

Cloning and Expression of the Human Gene Encoding hTRPM8 and Receptor Screen Using hTRPM8

The gene encoding hTRPM8 is the human ortholog of the rat cooling and menthol receptor (CMR) and of the mouse receptor TRPM8.

Human dorsal root ganglia total RNA (Stratagene, USA) is reverse transcribed using Superscript II (MMLV) Reverse Transcriptase (Invitrogen Inc., USA). The reaction is performed using 1 µg of total RNA as template and an oligo(dT) primer in a total volume of 20 µl, resulting in a cDNA product.

The coding region of the human TRPM8 cDNA (GenBank accession No. NM_024080) is amplified by PCR using primer No. 15 (5'-GATGTCCTTTCGGGCAGCCAGG-3) (hTMPR8-5-full) and primer No. 16 (5'-TTTATTTGATTT-TATTAGCAATCTC-3') (hTMPR8-3-full) that anneal to the ends of the coding sequence of hTRPM8. 1 µl of the cDNA product is used as template, and the PCR reaction is performed at an annealing temperature of 55° C. and an extension temperature of 72° C. in a volume of 25 µl for 35 cycles. The PCR product is purified using the QIAquick PCR Purification Kit columns (Qiagen, Germany) and cloned in the cloning vector pGEM-T (Promega Corp., USA).

The human hTRPM8 cDNA is subcloned in pcDNA5 (Invitrogen Inc., USA) and transfected into CHO-K1/FRT cells using Fugene (Roche, Switzerland) as described by Peier et al. (Cell (2002) 108:705-715) for mouse TRPM8 cDNA. The transfected CHO-K1/FRT cells are selected by growth in MEM medium containing 200 µg/ml hygromycin (Invitrogen Inc., USA). Stable CHO-K1/FRT cell clones that express the hTRPM8 mRNA are identified by Northern blot. The integration site of the cDNA in these clones is confirmed by Southern blot.

The stable CHO-K1/FRT cell clones that express hTRPM8 are used in a receptor screen to identify ligands of said receptor. This is performed analogous to the method described by Peier et al. (Cell (2002) 108:705-715) for the mouse TRPM8 cDNA. Glass coverslips, 24-well and 96-well tissue culture plates are used for cell plating. Cells are loaded with the calcium-sensitive fluorescent dye Fura-2 acetoxymethyl ester (Fura-2AM). As a test compound, menthol or another known ligand is diluted in a suitable buffer compatible with the CHO-K1/FRT cells. This sample is used in the receptor screen as described by Peier et al. The detection of a concentration dependent increase of intracellular calcium levels indicates the activation of hTRPM8 by its ligand.

Example 9

Incubation of Menthyl-lactate with Carboxyl Esterase and Identification of Metabolite as Receptor Ligand Menthyl-lactate, a substrate of CE, is incubated with CE. Controls contain menthyl-lactate but not CE. The incubation is performed as described in Examples 7B, subject to the following modifications: after 30 min incubation time at 25° C., the samples are chilled on ice for 10 min and centrifuged. Supernatants are transferred to empty wells and diluted with 1 volume 2×HEPES (4 mM $Ca^{2+}$). The dilution is used as a test sample in a receptor screen as described in Example 8.

If menthol is present in the test sample, an increase of intracellular calcium levels in hTRPM8-expressing CHO-K1 cells is detected. In controls with substrate but without CE and consequently without the metabolite menthol, no comparable increase can be detected. This shows that menthyl-lactate is not the main receptor ligand itself, but the metabolic reaction with CE forms menthol as a metabolite of menthyl-lactate, and the metabolite menthol is the preferred hTRPM8 agonist compared to menthyl lactate Example 10

Incubation of Octanol with Alcohol Dehydrogenase (ADH)

Human alcohol dehydrogenase exists as a heterogeneous group of isozymes capable of oxidizing a wide variety of aliphatic and aromatic alcohols. Any isozyme of the human enzyme can be used. In this example, equine liver ADH (EC 1.1.1.1; Sigma-Aldrich, Switzerland) is used instead of the human enzyme. Octanol is incubated with ADH in a 1-ml reaction volume containing 50 mM potassium phosphate (pH 8.5) and 10 mM NAD+ (Fluka, Switzerland). Octanol is added at a concentration of 0.1 M and the metabolic reaction is initiated by addition of 50 mU of ADH and incubated for 30 min at 25° C. The tube is centrifuged to separate any debris and the supernatant extracted with MTBE for analysis by GC and GC-MS. The reaction containing the enzyme is compared to the control and shows an additional peak when analysed by GC. The metabolite is identified by GC analysis and GC-MS as octanal.

Example 11

Incubation of Octanol with Alcohol Dehydrogenase and Identification of Metabolite as Receptor Ligand Octanol is incubated with alcohol dehydrogenase as described in example 10, controls without alcohol dehydrogenase are incubated accordingly. In the presence of the enzyme, the metabolite of octanol, which is octanal, is present as shown in example 10.

The rat olfactory receptor 17 together with the Galpha15, 16 are expressed by co-transfection in HEK293 cells as described by Krautwurst et al. (1998), Cell 95:917-926. Transfected HEK293 cells are plated on coverslips, 24-well tissue culture plates, and microtiter plates. These coverslips and plates are incubated with Fura-2 as described in example 8. The microtiter plates are incubated as described by Krautwurst et al. (1998).

Upon completion of the metabolic oxidation reaction (30 min reaction time as described in Example 10) the sample is chilled on ice for 10 min and centrifuged. The supernatant is transferred to an empty container and diluted with 2×HEPES (4 mM $Ca^{2+}$). This dilution is used as a sample in the receptor screen as described in Example 8, using HEK293 cells that express Galpha-15,16 and the rat olfactory receptor 17.

Fluorescence recording is performed to monitor any increase in intracellular, cytoplasmic calcium levels.

The increase in presence of octanal but not in presence of octanol (control without enzyme) shows that while octanol is not able to activate the receptor, its metabolite octanal is an agonist of the rat olfactory receptor 17.

Example 12

Incubation of Styrene Oxide with Human Microsomal Epoxide Hydrolase (EH) and Identification of a Metabolite 0.5 mM styrene oxide and 0.2 mg/ml EH (25,000 pmole styrene oxide hydrolase activity/(min×mg protein (BD Bioscience, Gentest, US)) in a 0.25 ml reaction mixture (0.1 M Tris-Cl, pH 9) is incubated for 30 min at 37° C. A control without enzyme is incubated accordingly. The reaction is stopped by adding 75 μl acetonitrile and placing the mixture on ice. The mixture is extracted with MTBE and analysed by GC-MS. A diol is found to be present in the sample but not in the control. A diol is formed from styrene epoxide that is hydrolysed to the corresponding diol.

Example 13

Incubation of Styrene with CYP2E1 and Epoxide Hydrolase (EH) Sequentially and Identification of Metabolites Styrene is incubated in a first incubation step with microsomal membranes of baculovirus-infected Sf9 insect cell membranes that contain CYP2E1 and POR. In a second incubation step, this sample is incubated with EH.

In the first step, 3 μl styrene (77 mM in acetonitrile), 425 μl potassium phosphate buffer (50 mM, pH 7.4), 16.5 μl $MgCl_2$, 50 pmole of CYP2E1 containing cytochrome P450 reductase (purchased from BD Bioscience, Gentest, US) and water are mixed to give a total volume of 470 μl. 30 μl NADPH (50 mM in water) are added to the sample, to the control 30 μl water are added. Sample and control are incubated at 37° C. for 1 hour.

In the second step, 50 μl of 1 M Tris-Cl, pH 9 followed by 0.4 mg/ml protein (human microsomal epoxide hydrolase microsomes, 25,000 pmole styrene oxide hydrolase activity/(min×mg protein) BD Bioscience, Gentest, US) is added and incubation is continued for 30 min.

After the second step, 100 μl acetonitrile is added to sample and control and they are placed on ice. This stops the enzymatic reaction. Compounds in the samples are extracted with MTBE.

Alternatively, the two enzymes can be incubated with styrene simultaneously. In this case, the following modifications apply: the buffer concentration is 100 mM potassium phosphate (pH 7.4), the second step is left out, and human microsomal epoxide hydrolase microsomes are added in the first step.

Metabolites, i.e. additional compounds present in the sample but not in the control, are identified by GC-MS. Identified metabolites are styrene epoxide and the corresponding diol. The styrene epoxide is formed by oxidation of styrene to styrene epoxide by CYP2E1. The diol is formed by further reaction of the first metabolite, styrene epoxide, with EH.

---

I claim:

1. An in-vitro method of identifying a metabolite of a test compound as a flavour or fragrance, the method comprising:
   a) reacting a test compound in-vitro in a reaction mixture with at least one isolated metabolic enzyme selected from the group consisting of dehydrogenase, Cytochrome P450 enzyme, epoxide hydrolase, esterase, flavin-containing monooxygenase, glutathione peroxidase, glutathione synthase, glutathione S-transferase, oxidase, reductase, rhodanese, sulfatase, sulfotransferase, UDP-glucuronosyltransferase, carboxyl esterase, and mixtures thereof, wherein the test compound is metabolizable by said at least one metabolic enzyme; and
   b) subsequent to said metabolic reaction separating the test compound and the metabolites from said reaction mixture, and identifying if at least one metabolite of the test compound is a fragrance or flavour by using an in-vitro chemoreceptor screen that is capable of detecting said fragrance or flavour.

2. The method according to claim 1 wherein the metabolic enzyme is a Cytochrome P450 enzyme.

3. The method according to claim 2 wherein the Cytochrome P450 enzyme is selected from the group consisting of CYP1A1, CYP1A2, CYP1B1, CYP2B4, CYP2B6, CYP2A6, CYP2A7, CYP2A13, CYP2B1, CYP2B6, CYP2CS, CYP2C9, CYP2C18, CYP2C19, CYP2C39, CYP2D6, CYP2E1, CYP2F1, CYP2J2, CYP2S1, CYP3A4, CYP3AS, CYP3A7, CYP4A, CYP4A11, CYP 4B1, CYP4B1Ser207, CYP4F2, CYP4F3A, CYP4F3B, CYP4F12, CYPS1, CYP11A1, CYP19, P450 IID, P450 HFLa, and mixtures thereof.

4. The method according to claim 3 wherein one or more of the Cytochrome P450 enzymes is a polymorphic form of said enzymes.

5. The method according to claim 1, wherein the metabolic enzyme is selected from the group consisting of CYP2A13, CYP2E1, carboxyl esterase, alcohol dehydrogenase, epoxide hydrolase, and mixtures thereof.

6. The method according to claims 1 to 5, wherein the step of identifying the metabolite having a flavour or fragrance further comprises a sensory method employing one or more human test subjects.

7. The method according to claim 6 wherein metabolites are identified using gas chromatography-olfactometry (GC-sniff), or an olfactometer.

8. The method according to any one of claims 1 to 5, further comprises a physical-chemical analysis by one or more methods selected from the group consisting of gas chromatography, gas-chromatography and mass spectroscopy, liquid chromatography, and mass spectroscopy.

9. The method according to any one of the claims 1 to 5, wherein the step of reacting the test compound with at least one isolated metabolic enzyme is performed in presence of a standard substrate or a standard product.

10. The method according to claim 9 wherein the standard substrate or the standard product is fluorescent.

11. The method according to any one of claims 1 to 5 wherein the chemoreceptor screen uses a chemoreceptor selected from the group consisting of a olfactory receptor, a gustatory receptor, and a cooling receptor.

* * * * *

UNITED STATES PATENT AND TRADEMARK OFFICE
CERTIFICATE OF CORRECTION

Page 1 of 1

PATENT NO. : 9,012,169 B2
APPLICATION NO. : 11/632977
DATED : April 21, 2015
INVENTOR(S) : Boris Schilling It is certified that error appears in the above-identified patent and that said Letters Patent is hereby corrected as shown below:

In the Claims,

In claim 3, column 47, lines 23-32, the group from which Cytochrome P450 enzyme is selected is incorrect. The group at column 47, lines 23-32 should read, "the group consisting of CYP1A1, CYP1A2, CYP1B1, CYP2B4, CYP2B6, CYP2A6, CYP2A7, CYP2A13, CYP2B1, CYP2B6, CYP2C8, CYP2C9, CYP2C18, CYP2C19, CYP2C39, CYP2D6, CYP2E1, CYP2F1, CYP2J2, CYP2S1, CYP3A4, CYP3A5, CYP3A7, CYP4A, CYP4A11, CYP 4B1, CYP4B1Ser207, CYP4F2, CYP4F3A, CYP4F3B, CYP4F12, CYP51, CYP11A1, CYP19, P450 IID, P450 HFLa, and mixtures thereof."

Signed and Sealed this
Twenty-fifth Day of August, 2015

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
atatccttag gcgactgagg                                                    20

<210> SEQ ID NO 2
<211> LENGTH: 18
<212> TYPE: DNA
<213> ORGANISM: Artificial
<220> FEATURE:
<223> OTHER INFORMATION: primer

<400> SEQUENCE: 2
cagggctgct tctggtga                                                      18

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
atatccttag gcgactgagg                                                    20

<210> SEQ ID NO 4
<211> LENGTH: 20
<212> TYPE: DNA
<213> ORGANISM: Artificial
```

<220> FEATURE:
<223> OTHER INFORMATION: primer

<400> SEQUENCE: 4
gtcttgatgt cagtctggcg                                              20

<210> SEQ ID NO 5
<211> LENGTH: 52
<212> TYPE: DNA
<213> ORGANISM: Artificial
<220> FEATURE:
<223> OTHER INFORMATION: primer

<400> SEQUENCE: 5
tctggtgacc ttgctggcct gcctgactgt gatggtcttg atgtctgttt gg          52

<210> SEQ ID NO 6
<211> LENGTH: 60
<212> TYPE: DNA
<213> ORGANISM: Artificial
<220> FEATURE:
<223> OTHER INFORMATION: primer

<400> SEQUENCE: 6
gggatcgtgg caaagcccac gtgtttgggg gacacgtcaa tgtccttagg cgactgagga  60

<210> SEQ ID NO 7
<211> LENGTH: 50
<212> TYPE: DNA
<213> ORGANISM: Artificial
<220> FEATURE:
<223> OTHER INFORMATION: primer

<400> SEQUENCE: 7
tatgaattct atgctggcct cagggctgct tctggtgacc ttgctggcct              50

<210> SEQ ID NO 8
<211> LENGTH: 62
<212> TYPE: DNA
<213> ORGANISM: Artificial
<220> FEATURE:
<223> OTHER INFORMATION: primer

<400> SEQUENCE: 8
agaagcttat cagcggggca ggaagctcat ggtgtagttt cgtgggatcg tggcaaagcc  60
ca                                                                 62

<210> SEQ ID NO 9
<211> LENGTH: 19
<212> TYPE: DNA
<213> ORGANISM: Artificial
<220> FEATURE:
<223> OTHER INFORMATION: primer

<400> SEQUENCE: 9
gatgtctgcc ctcggagtg                                               19

<210> SEQ ID NO 10
<211> LENGTH: 19
<212> TYPE: DNA
<213> ORGANISM: Artificial
<220> FEATURE:
<223> OTHER INFORMATION: primer

```
<400> SEQUENCE: 10
ctcatgagcg gggaatgac                                                    19

<210> SEQ ID NO 11
<211> LENGTH: 18
<212> TYPE: DNA
<213> ORGANISM: Artificial
<220> FEATURE:
<223> OTHER INFORMATION: primer

<400> SEQUENCE: 11
ctacaaggac gagttctc                                                     18

<210> SEQ ID NO 12
<211> LENGTH: 18
<212> TYPE: DNA
<213> ORGANISM: Artificial
<220> FEATURE:
<223> OTHER INFORMATION: primer

<400> SEQUENCE: 12
gagttggcac tacgactg                                                     18

<210> SEQ ID NO 13
<211> LENGTH: 22
<212> TYPE: DNA
<213> ORGANISM: Artificial
<220> FEATURE:
<223> OTHER INFORMATION: primer

<400> SEQUENCE: 13
gatgtggctc cgtgccttta tc                                                22

<210> SEQ ID NO 14
<211> LENGTH: 24
<212> TYPE: DNA
<213> ORGANISM: Artificial
<220> FEATURE:
<223> OTHER INFORMATION: primer

<400> SEQUENCE: 14
cttcattcac agctctatgt gttc                                              24

<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15
gatgtccttt cgggcagcca gg                                                22

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
tttatttgat tttattagca atctc                                             25
```